(12) United States Patent
Foster et al.

(10) Patent No.: US 10,743,942 B2
(45) Date of Patent: Aug. 18, 2020

(54) COSMETIC AND THERAPEUTIC INJECTION SAFETY SYSTEMS, METHODS, AND DEVICES

(71) Applicant: TruInject Medical Corp., Irvine, CA (US)

(72) Inventors: Clark B. Foster, Mission Viejo, CA (US); Gabrielle A. Rios, Irvine, CA (US)

(73) Assignee: Truinject Corp., Irvine, CA (US)

( * ) Notice: Subject to any disclaimer, the term of this patent is extended or adjusted under 35 U.S.C. 154(b) by 340 days.

(21) Appl. No.: 15/444,143

(22) Filed: Feb. 27, 2017

(65) Prior Publication Data

US 2017/0245943 A1    Aug. 31, 2017

Related U.S. Application Data

(60) Provisional application No. 62/301,462, filed on Feb. 29, 2016, provisional application No. 62/303,251, filed on Mar. 3, 2016.

(51) Int. Cl.
*A61B 34/20* (2016.01)
*A61B 5/00* (2006.01)
(Continued)

(52) U.S. Cl.
CPC ............ *A61B 34/20* (2016.02); *A61B 5/0077* (2013.01); *A61B 5/0082* (2013.01);
(Continued)

(58) Field of Classification Search
CPC ..... A61B 5/0205; A61B 5/021; A61B 5/0215; A61B 5/02108; A61B 5/02116;
(Continued)

(56) References Cited

U.S. PATENT DOCUMENTS 3,237,340 A    3/1966 Knott
3,941,121 A    3/1976 Olinger et al.
(Continued)

FOREIGN PATENT DOCUMENTS

AU    2011218649 B2    9/2011
AU    2015255197 A1    12/2015
(Continued)

OTHER PUBLICATIONS

Correa et al., "Virtual Reality Simulator for Dental Anesthesia Training in the Inferior Alveolar Nerve Block," Journal of Applied Oral Science, vol. 25, No. 4, Jul./Aug. 2017.
(Continued)

*Primary Examiner* — Robert A Lynch
(74) *Attorney, Agent, or Firm* — Knobbe, Martens, Olson & Bear, LLP

(57) ABSTRACT

A system for providing a real-time indication of a location of the distal tip of a medical device in living tissue. The system may include an injection scanning printer that provides a visual indication of detected features to improve the injecting process. Safety needles configured to detect nerves, arteries, veins, or other physiological features upon needle placement but prior to injecting are also provided.

14 Claims, 16 Drawing Sheets

(51) Int. Cl.

| | | |
|---|---|---|
| *A61M 5/00* | (2006.01) | |
| *A61M 1/00* | (2006.01) | |
| *A61M 5/158* | (2006.01) | |
| *A61M 5/42* | (2006.01) | |
| *A61M 5/46* | (2006.01) | |
| *A61B 90/00* | (2016.01) | |
| *A61B 90/30* | (2016.01) | |
| *A61B 90/50* | (2016.01) | |

(52) U.S. Cl.
CPC ............ *A61B 5/6842* (2013.01); *A61M 1/008* (2013.01); *A61M 5/00* (2013.01); *A61M 5/158* (2013.01); *A61M 5/427* (2013.01); *A61M 5/46* (2013.01); *A61B 5/441* (2013.01); *A61B 2034/2048* (2016.02); *A61B 2034/2055* (2016.02); *A61B 2034/2057* (2016.02); *A61B 2034/2074* (2016.02); *A61B 2090/309* (2016.02); *A61B 2090/365* (2016.02); *A61B 2090/395* (2016.02); *A61B 2090/3937* (2016.02); *A61B 2090/502* (2016.02); *A61M 2205/3303* (2013.01); *A61M 2205/3507* (2013.01)

(58) Field of Classification Search
CPC ............ A61B 5/02125; A61B 5/02141; A61B 5/150801; A61B 5/150824; A61B 5/4887; A61B 5/489; A61B 5/68; A61B 5/6802; A61B 5/742; A61M 25/06
See application file for complete search history.

(56) References Cited

U.S. PATENT DOCUMENTS

| | | |
|---|---|---|
| 4,142,517 A | 3/1979 | Contreras Guerrero de Stavropoulos et al. |
| 4,311,138 A | 1/1982 | Sugarman |
| 4,356,828 A | 11/1982 | Jamshidi |
| 4,410,020 A | 10/1983 | Lorenz |
| 4,515,168 A | 5/1985 | Chester et al. |
| 4,566,438 A | 1/1986 | Liese et al. |
| 4,836,632 A | 6/1989 | Bardoorian |
| 4,867,686 A | 9/1989 | Goldstein |
| 4,880,971 A | 11/1989 | Danisch |
| 5,065,236 A | 11/1991 | Diner |
| 5,197,476 A | 3/1993 | Nowacki et al. |
| 5,198,877 A | 3/1993 | Schulz |
| 5,241,184 A | 8/1993 | Menzel |
| 5,249,581 A | 10/1993 | Horbal et al. |
| 5,295,483 A | 3/1994 | Nowacki et al. |
| 5,321,257 A | 6/1994 | Danisch |
| 5,391,081 A | 2/1995 | Lampotang et al. |
| 5,517,997 A | 5/1996 | Fontenot |
| 5,518,407 A | 5/1996 | Greenfield et al. |
| 5,534,704 A | 7/1996 | Robinson et al. |
| 5,622,170 A | 4/1997 | Shulz |
| 5,651,783 A | 7/1997 | Reynard |
| 5,690,618 A | 11/1997 | Smith et al. |
| 5,727,948 A | 3/1998 | Jordan |
| 5,817,105 A | 10/1998 | Van Der Brug |
| 5,828,770 A | 10/1998 | Leis et al. |
| 5,890,908 A | 4/1999 | Lampotang et al. |
| 5,899,692 A | 5/1999 | Davis et al. |
| 5,923,417 A | 7/1999 | Leis |
| 5,954,648 A | 9/1999 | Van Der Brug |
| 5,954,701 A | 9/1999 | Matalon |
| 6,024,576 A | 2/2000 | Bevirt et al. |
| 6,061,644 A | 5/2000 | Leis |
| 6,064,749 A | 5/2000 | Hirota et al. |
| 6,127,672 A | 10/2000 | Danisch |
| 6,217,558 B1 | 4/2001 | Zadini et al. |
| 6,288,785 B1 | 9/2001 | Frantz et al. |
| 6,353,226 B1 | 3/2002 | Khalil et al. |
| 6,385,482 B1 | 5/2002 | Boksberger et al. |
| 6,485,308 B1 | 11/2002 | Goldstein |
| 6,553,326 B1 | 4/2003 | Kirsch et al. |
| 6,564,087 B1 | 5/2003 | Pitris et al. |
| 6,575,757 B1 | 6/2003 | Leight et al. |
| 6,625,563 B2 | 9/2003 | Kirsch et al. |
| 6,702,790 B1 | 3/2004 | Ross et al. |
| 6,769,286 B2 | 8/2004 | Biermann et al. |
| 6,774,624 B2 | 8/2004 | Anderson et al. |
| 6,836,745 B2 | 12/2004 | Seiler et al. |
| 6,863,536 B1 | 3/2005 | Fisher et al. |
| 7,015,859 B2 | 3/2006 | Anderson |
| 7,115,113 B2 | 10/2006 | Evans et al. |
| 7,137,712 B2 | 11/2006 | Brunner et al. |
| 7,158,754 B2 | 1/2007 | Anderson |
| 7,194,296 B2 | 3/2007 | Frantz et al. |
| 7,204,796 B1 | 4/2007 | Seiler |
| 7,247,149 B2 | 7/2007 | Beyerlein |
| 7,383,728 B2 | 6/2008 | Noble et al. |
| 7,500,853 B2 | 3/2009 | Bevirt et al. |
| 7,553,159 B1 | 6/2009 | Arnal et al. |
| 7,594,815 B2 | 9/2009 | Toly |
| 7,665,995 B2 | 2/2010 | Toly |
| 7,725,279 B2 | 5/2010 | Luinge et al. |
| 7,761,139 B2 | 7/2010 | Tearney et al. |
| 7,783,441 B2 | 8/2010 | Nieminen et al. |
| 7,857,626 B2 | 12/2010 | Toly |
| 7,912,662 B2 | 3/2011 | Zuhars et al. |
| 7,945,311 B2 | 5/2011 | McCloy et al. |
| 8,007,281 B2 | 8/2011 | Toly |
| 8,040,127 B2 | 10/2011 | Jensen |
| 8,072,606 B2 | 12/2011 | Chau et al. |
| 8,131,342 B2 | 3/2012 | Anderson |
| 8,165,844 B2 | 4/2012 | Luinge et al. |
| 8,203,487 B2 | 6/2012 | Hol et al. |
| 8,208,716 B2 | 6/2012 | Choi et al. |
| 8,226,610 B2 | 7/2012 | Edwards et al. |
| 8,250,921 B2 | 8/2012 | Nasiri et al. |
| 8,257,250 B2 | 9/2012 | Tenger et al. |
| 8,277,411 B2 | 10/2012 | Gellman |
| 8,319,182 B1 | 11/2012 | Brady et al. |
| 8,342,853 B2 | 1/2013 | Cohen |
| 8,351,773 B2 | 1/2013 | Nasiri et al. |
| 8,382,485 B2 | 2/2013 | Bardsley |
| 8,403,888 B2 | 3/2013 | Gaudet |
| 8,408,918 B2 | 4/2013 | Hu et al. |
| 8,409,140 B2 | 4/2013 | Ejlersen et al. |
| 8,437,833 B2 | 5/2013 | Silverstein |
| 8,442,619 B2 | 5/2013 | Li et al. |
| 8,450,997 B2 | 5/2013 | Silverman |
| 8,467,855 B2 | 6/2013 | Yasui |
| 8,525,990 B2 | 9/2013 | Wilcken |
| 8,535,062 B2 | 9/2013 | Nguyen |
| 8,556,635 B2 | 10/2013 | Toly |
| 8,632,498 B2 | 1/2014 | Rimsa et al. |
| 8,655,622 B2 | 2/2014 | Yen et al. |
| 8,689,801 B2 | 4/2014 | Ritchey et al. |
| 8,764,449 B2 | 7/2014 | Rios et al. |
| 8,818,751 B2 | 8/2014 | Van Acht et al. |
| 8,917,916 B2 | 12/2014 | Martin et al. |
| 8,945,147 B2 | 2/2015 | Ritchey et al. |
| 8,961,189 B2 | 2/2015 | Rios et al. |
| 8,994,366 B2 | 3/2015 | Ashe |
| 9,017,080 B1 | 4/2015 | Placik |
| 9,024,624 B2 | 5/2015 | Brunner |
| 9,031,314 B2 | 5/2015 | Clausen et al. |
| 9,251,721 B2 | 2/2016 | Lampotang et al. |
| 9,439,653 B2 | 9/2016 | Avneri et al. |
| 9,443,446 B2 | 9/2016 | Rios et al. |
| 9,456,766 B2 | 10/2016 | Cox et al. |
| 9,460,638 B2 | 10/2016 | Baker et al. |
| 9,486,162 B2 | 11/2016 | Zhuang et al. |
| 9,626,805 B2 | 4/2017 | Lampotang et al. |
| 9,792,836 B2 | 10/2017 | Rios et al. |
| 9,922,578 B2 | 3/2018 | Foster et al. |
| 10,269,266 B2 | 4/2019 | Rios et al. |
| 10,290,231 B2 | 5/2019 | Rios et al. |
| 10,290,232 B2 | 5/2019 | Rios et al. |
| 10,500,340 B2 | 12/2019 | Rios et al. |
| 2002/0168618 A1 | 11/2002 | Anderson et al. |

(56) References Cited

U.S. PATENT DOCUMENTS

| | | |
|---|---|---|
| 2002/0191000 A1 | 12/2002 | Henn |
| 2003/0031993 A1 | 2/2003 | Pugh |
| 2003/0055380 A1 | 3/2003 | Flaherty |
| 2003/0108853 A1 | 6/2003 | Chosack et al. |
| 2003/0114842 A1 | 6/2003 | DiStefano |
| 2003/0220557 A1 | 11/2003 | Cleary et al. |
| 2004/0009459 A1 | 1/2004 | Anderson et al. |
| 2004/0092878 A1 | 5/2004 | Flaherty |
| 2004/0118225 A1 | 6/2004 | Wright et al. |
| 2004/0126746 A1 | 7/2004 | Toly |
| 2004/0175684 A1 | 9/2004 | Kaasa et al. |
| 2005/0055241 A1 | 3/2005 | Horstmann |
| 2005/0057243 A1 | 3/2005 | Johnson et al. |
| 2005/0084833 A1 | 4/2005 | Lacey et al. |
| 2005/0181342 A1 | 8/2005 | Toly |
| 2005/0203380 A1 | 9/2005 | Sauer et al. |
| 2006/0084050 A1 | 4/2006 | Haluck |
| 2006/0194180 A1 | 8/2006 | Bevirt et al. |
| 2006/0264745 A1 | 11/2006 | Da Silva |
| 2006/0264967 A1 | 11/2006 | Ferreyro et al. |
| 2007/0003917 A1 | 1/2007 | Kitching et al. |
| 2007/0179448 A1 | 8/2007 | Lim et al. |
| 2007/0197954 A1 | 8/2007 | Keenan |
| 2008/0097378 A1 | 4/2008 | Zuckerman |
| 2008/0107305 A1 | 5/2008 | Vanderkooy et al. |
| 2008/0123910 A1 | 5/2008 | Zhu |
| 2008/0138781 A1 | 6/2008 | Pellegrin et al. |
| 2008/0176198 A1 | 7/2008 | Ansari et al. |
| 2009/0036902 A1 | 2/2009 | Dimaio et al. |
| 2009/0043253 A1 | 2/2009 | Podaima |
| 2009/0046140 A1 | 2/2009 | Lashmet |
| 2009/0061404 A1 | 3/2009 | Toly |
| 2009/0074262 A1 | 3/2009 | Kudavelly |
| 2009/0081619 A1 | 3/2009 | Miasnik |
| 2009/0081627 A1 | 3/2009 | Ambrozio |
| 2009/0123896 A1 | 5/2009 | Hu et al. |
| 2009/0142741 A1 | 6/2009 | Ault et al. |
| 2009/0161827 A1 | 6/2009 | Gertner et al. |
| 2009/0208915 A1 | 8/2009 | Pugh |
| 2009/0263775 A1 | 10/2009 | Ullrich |
| 2009/0265671 A1 | 10/2009 | Sachs et al. |
| 2009/0275810 A1* | 11/2009 | Ayers .................... A61B 5/0205 600/301 |
| 2009/0278791 A1 | 11/2009 | Slycke et al. |
| 2009/0305213 A1 | 12/2009 | Burgkart et al. |
| 2009/0326556 A1 | 12/2009 | Diolaiti |
| 2010/0030111 A1 | 2/2010 | Perriere |
| 2010/0071467 A1 | 3/2010 | Nasiri et al. |
| 2010/0099066 A1 | 4/2010 | Mire et al. |
| 2010/0120006 A1 | 5/2010 | Bell |
| 2010/0167249 A1 | 7/2010 | Ryan |
| 2010/0167254 A1 | 7/2010 | Nguyen |
| 2010/0179428 A1 | 7/2010 | Pederson et al. |
| 2010/0198141 A1 | 8/2010 | Laitenberger et al. |
| 2010/0273135 A1 | 10/2010 | Cohen |
| 2011/0027767 A1 | 2/2011 | Divinagracia |
| 2011/0046915 A1 | 2/2011 | Hol et al. |
| 2011/0060229 A1* | 3/2011 | Hulvershorn ........ A61B 5/0215 600/486 |
| 2011/0071419 A1 | 3/2011 | Liu et al. |
| 2011/0144658 A1 | 6/2011 | Wenderow et al. |
| 2011/0202012 A1 | 8/2011 | Bartlett |
| 2011/0207102 A1 | 8/2011 | Trotta et al. |
| 2011/0236866 A1 | 9/2011 | Psaltis et al. |
| 2011/0257596 A1 | 10/2011 | Gaudet |
| 2011/0269109 A2 | 11/2011 | Miyazaki |
| 2011/0282188 A1 | 11/2011 | Burnside et al. |
| 2011/0294103 A1 | 12/2011 | Segal et al. |
| 2011/0301500 A1 | 12/2011 | Maguire et al. |
| 2011/0306025 A1 | 12/2011 | Sheehan et al. |
| 2012/0002014 A1 | 1/2012 | Walsh |
| 2012/0015336 A1 | 1/2012 | Mach |
| 2012/0026307 A1 | 2/2012 | Price |
| 2012/0034587 A1 | 2/2012 | Toly |
| 2012/0130269 A1 | 5/2012 | Rea |
| 2012/0148994 A1 | 6/2012 | Hori et al. |
| 2012/0171652 A1 | 7/2012 | Sparks et al. |
| 2012/0183238 A1 | 7/2012 | Savvides et al. |
| 2012/0209243 A1 | 8/2012 | Yan |
| 2012/0214144 A1 | 8/2012 | Trotta et al. |
| 2012/0219937 A1 | 8/2012 | Hughes |
| 2012/0238875 A1 | 9/2012 | Savitsky et al. |
| 2012/0251987 A1 | 10/2012 | Huang et al. |
| 2012/0280988 A1 | 11/2012 | Lampotang et al. |
| 2012/0282583 A1 | 11/2012 | Thaler et al. |
| 2012/0293632 A1 | 11/2012 | Yukich |
| 2012/0301858 A1 | 11/2012 | Park et al. |
| 2012/0323520 A1 | 12/2012 | Keal |
| 2013/0006178 A1 | 1/2013 | Pinho et al. |
| 2013/0018494 A1 | 1/2013 | Amini |
| 2013/0046489 A1 | 2/2013 | Keal |
| 2013/0100256 A1 | 4/2013 | Kirk et al. |
| 2013/0131503 A1 | 5/2013 | Schneider et al. |
| 2013/0179110 A1 | 7/2013 | Lee |
| 2013/0189658 A1 | 7/2013 | Peters et al. |
| 2013/0197845 A1 | 8/2013 | Keal |
| 2013/0198625 A1 | 8/2013 | Anderson |
| 2013/0203032 A1 | 8/2013 | Bardsley |
| 2013/0223673 A1 | 8/2013 | Davis et al. |
| 2013/0236872 A1 | 9/2013 | Laurusonis et al. |
| 2013/0267838 A1* | 10/2013 | Fronk .................... A61B 5/066 600/424 |
| 2013/0296691 A1 | 11/2013 | Ashe |
| 2013/0308827 A1 | 11/2013 | Dillavou et al. |
| 2013/0323700 A1 | 12/2013 | Samosky et al. |
| 2013/0342657 A1 | 12/2013 | Robertson |
| 2014/0039452 A1 | 2/2014 | Bangera et al. |
| 2014/0102167 A1 | 4/2014 | MacNeil et al. |
| 2014/0120505 A1 | 5/2014 | Rios et al. |
| 2014/0121636 A1 | 5/2014 | Boyden |
| 2014/0162232 A1 | 6/2014 | Yang et al. |
| 2014/0212864 A1 | 7/2014 | Rios et al. |
| 2014/0240314 A1 | 8/2014 | Fukazawa et al. |
| 2014/0244209 A1 | 8/2014 | Lee et al. |
| 2014/0260704 A1 | 9/2014 | Lloyd et al. |
| 2014/0278183 A1 | 9/2014 | Zheng et al. |
| 2014/0278205 A1 | 9/2014 | Bhat et al. |
| 2014/0278215 A1 | 9/2014 | Keal et al. |
| 2014/0322683 A1 | 10/2014 | Baym et al. |
| 2014/0349266 A1 | 11/2014 | Choi |
| 2015/0079545 A1 | 3/2015 | Kurtz |
| 2015/0086955 A1 | 3/2015 | Poniatowski et al. |
| 2015/0182706 A1 | 7/2015 | Wurmbauer et al. |
| 2015/0206456 A1 | 7/2015 | Foster et al. |
| 2015/0262512 A1 | 9/2015 | Rios et al. |
| 2015/0352294 A1 | 12/2015 | O'Mahoney et al. |
| 2015/0379899 A1 | 12/2015 | Baker et al. |
| 2015/0379900 A1 | 12/2015 | Samosky et al. |
| 2016/0000411 A1 | 1/2016 | Raju et al. |
| 2016/0001016 A1 | 1/2016 | Poulsen et al. |
| 2016/0155363 A1 | 6/2016 | Rios et al. |
| 2016/0193428 A1 | 7/2016 | Perthu |
| 2016/0213856 A1 | 7/2016 | Despa et al. |
| 2016/0293058 A1 | 10/2016 | Gaillot et al. |
| 2016/0374902 A1 | 12/2016 | Govindasamy et al. |
| 2017/0053563 A1 | 2/2017 | Holloway |
| 2017/0136185 A1 | 5/2017 | Rios et al. |
| 2017/0178540 A1 | 6/2017 | Rios et al. |
| 2017/0186339 A1 | 6/2017 | Rios et al. |
| 2017/0252108 A1 | 9/2017 | Rios et al. |
| 2017/0254636 A1 | 9/2017 | Foster et al. |
| 2017/0316720 A1 | 11/2017 | Singh et al. |
| 2018/0012516 A1 | 1/2018 | Rios et al. |
| 2018/0068075 A1 | 3/2018 | Shiwaku |
| 2018/0197441 A1 | 7/2018 | Rios et al. |
| 2018/0225991 A1 | 8/2018 | Pedroso et al. |
| 2018/0240365 A1 | 8/2018 | Foster et al. |
| 2018/0261125 A1 | 9/2018 | Rios et al. |
| 2018/0261126 A1 | 9/2018 | Rios et al. |

(56) References Cited

U.S. PATENT DOCUMENTS

2018/0333543 A1 11/2018 Diaz et al.
2019/0130792 A1 5/2019 Rios et al.

FOREIGN PATENT DOCUMENTS

| | | |
|---|---|---|
| CA | 2865236 A1 | 9/2013 |
| CN | 2751386 Y | 1/2006 |
| CN | 201213049 Y | 3/2009 |
| CN | 102708745 A | 10/2012 |
| CN | 104703641 A | 6/2015 |
| CN | 105118350 A | 12/2015 |
| CN | 205541594 U | 8/2016 |
| CN | 106710413 A | 5/2017 |
| CN | 107067856 A | 8/2017 |
| DE | 202005021286 U1 | 9/2007 |
| EP | 0316763 A1 | 5/1989 |
| EP | 1504713 A1 | 2/2005 |
| EP | 1723977 A1 | 11/2006 |
| EP | 1884211 A2 | 2/2008 |
| EP | 2425416 B1 | 3/2015 |
| EP | 2538398 B1 | 8/2015 |
| EP | 2756857 B1 | 5/2016 |
| GB | 2288686 B | 7/1997 |
| GB | 2309644 A | 8/1997 |
| GB | 2508510 | 6/2014 |
| IN | 201202900 P1 | 11/2013 |
| JP | 2013-037088 A | 2/2013 |
| JP | 52-21420 | 6/2013 |
| JP | 2013-250453 A | 12/2013 |
| JP | 2014-153482 A | 8/2014 |
| KR | 2012009379 A | 2/2012 |
| KR | 20140047943 A | 4/2014 |
| KR | 10-1397522 B1 | 5/2014 |
| TW | 201207785 A | 2/2012 |
| WO | WO 00/53115 | 9/2000 |
| WO | WO 02/083003 | 10/2002 |
| WO | WO 2005/083653 | 9/2005 |
| WO | WO 2007/109540 | 9/2007 |
| WO | WO 2008/005315 A2 | 1/2008 |
| WO | WO 2008/122006 A1 | 10/2008 |
| WO | WO 2009/023247 A1 | 2/2009 |
| WO | WO 2009/049282 | 4/2009 |
| WO | WO 2009/094646 | 7/2009 |
| WO | WO 2009/141769 | 11/2009 |
| WO | WO 2011/043645 | 4/2011 |
| WO | WO 2011/127379 | 10/2011 |
| WO | WO 2011/136778 | 11/2011 |
| WO | WO 2012/075166 | 6/2012 |
| WO | WO 2012/088471 A1 | 6/2012 |
| WO | WO 2012/101286 | 8/2012 |
| WO | WO 2012/106706 | 8/2012 |
| WO | WO 2012/155056 | 11/2012 |
| WO | WO 2013/025639 | 2/2013 |
| WO | WO 2013/064804 A1 | 5/2013 |
| WO | WO 2014/070799 | 5/2014 |
| WO | WO 2014/100658 | 6/2014 |
| WO | WO 2015/109251 | 7/2015 |
| WO | WO 2015/110327 A1 | 7/2015 |
| WO | WO 2015/136564 | 9/2015 |
| WO | WO 2015/138608 | 9/2015 |
| WO | WO 2015/171778 | 11/2015 |
| WO | WO 2016/089706 | 6/2016 |
| WO | WO 2016/123144 A2 | 8/2016 |
| WO | WO 2016/162298 | 10/2016 |
| WO | WO 2016/191127 | 12/2016 |
| WO | WO 2017/048929 A1 | 3/2017 |
| WO | WO 2017/048931 A1 | 3/2017 |
| WO | WO 2017/050781 A1 | 3/2017 |
| WO | WO 2017/060017 A1 | 4/2017 |
| WO | WO 2017/070391 | 4/2017 |
| WO | WO 2017/151441 | 9/2017 |
| WO | WO 2017/151716 | 9/2017 |
| WO | WO 2017/151963 | 9/2017 |
| WO | WO 2017/153077 | 9/2017 |
| WO | WO 2018/136901 | 7/2018 |

OTHER PUBLICATIONS

Garg et al., "Radial Artery cannulation—Prevention of pain and Techniques of cannulation: review of literature," The Internet Journal of Anesthesiology, vol. 19, No. 1, 2008, in 6 pages.

International Search Report and Written Opinion for Appl. No. PCT/US2017/019518, dated Sep. 18, 2017, 19 pages.

Jafarzadeh et al., "Design and construction of an automatic syringe injection pump," Pacific Science Review A: Natural Science and Engineering 18, 2016, in 6 pages.

Kettenbach et al., "A robotic needle-positioning and guidance system for CT-guided puncture: Ex vivo results," Minimally Invasive Therapy and Allied Technologies, vol. 23, 2014, in 8 pages.

Ladjal, et al., "Interactive Cell Injection Simulation Based on 3D Biomechanical Tensegrity Model," 2008 IEEE/RSJ International Conference on Intelligent Robots and Systems, in 9 pages.

Lee et al., "An Intravenous Injection Simulator Using Augmented Reality for Veterinary Education and its Evaluation," Proceedings of the 11th ACM SIGGRAPH International Conference on Virtual-Reality Continuum and its Applications in Industry, Dec. 2-4, 2012, in 4 pages.

Poyade et al., "Development of a Haptic Training Simulation for the Administration of Dental Anesthesia Based Upon Accurate Anatomical Data," Conference and Exhibition of the European Association of Virtual and Augmented Reality, 2014, in 5 pages.

Quio, "Smartinjector," available at https://web.archive.org/web/20161017192142/http://www.quio.com/smartinjector, Applicant believes to be available as early as Oct. 17, 2016, in 3 pages.

State Electronics, "Sensofoil Membrane Potentiometer," Product Information and Technical Specifications.

Truinject Corp., "Smart Injection Platform," http://truinject.com/technology/, in 3 pages.

Bergamini et al., "Estimating Orientation Using Magnetic and Inertial Sensors and Different Sensor Fusion Approaches: Accuracy Assessment in Manual and Locomotion Tasks", Oct. 2014, 18625-18649.

Desjardins, et al. "Epidural needle with embedded optical fibers for spectroscopic differentiation of tissue: ex vivo feasibility study", Biomedical Optics Express, vol. 2(6): pp. 1-10. Jun. 2011.

"The EpiAccess System: Access with Confidence", EpiEP Epicardial Solutions, dated 2015, in 2 pages.

Afzal, et al., "Use of Earth's Magnetic Field for Mitigating Gyroscope Errors Regardless of Magnetic Perturbation," Sensors 2011, 11, 11390-11414; doi:10.3390/s111211390, 25 pp. published Nov. 30, 2011.

Andraos et al., "Sensing your Orientation" Address 2007, 7 pp.

Arms, S.W., "A Vision for Future Wireless Sensing Systems," 44 pp., 2003.

Bao, et al., "A Novel Map-Based Dead-Reckoning Algorithm for Indoor Localization", J. Sens. Actuator Netw, 2014, 3, 44-63; doi:10.3390/jsan3010044, 20 pp., Jan. 3, 2014.

Benbasat et al., "An Inertial Measurement Framework for Gesture Recognition and Applications," I. Wachsmuth and T. Sowa (Eds.): GW 2001, Springer-Verlag Berlin Heidelberg, 12 pp., 2002.

Brunet et al., "Uncalibrated Stereo Vision," A CS 766 Project, University of Wisconsin—Madison, 6 pp, Fall 2004, http://pages.cs.wisc.edu/~chaol/cs766/.

Brunet et al., "Uncalibrated Stereo Vision," A CS 766 Project, University of Wisconsin—Madison, 13 pp, Fall 2004, http://pages.cs.wisc.edu/~chaol/cs766/.

"EPGL Medical Invents Smart Epidural Needle, Nerve Ablation and Trigger Point Treatment Devices: New Smart Medical Devices Will Give Physicians Advanced Situational Awareness During Critical Procedures," EPGL Medical, dated Aug. 12, 2013, in 3 pages. Retreived from http://www.prnewswire.com/news-releases/epgl-medical-invents-smart-epidural-needle-nerve-ablation-and-trigger-point-treatment-devices-219344621.html#.

Esteve, Eric, "Why do you need 9D Sensor Fusion to support 3D orientation?", 5 pp., Aug. 23, 2014, https://www.semiwiki.com/forum/content/3794-why-do-you-need-9d-sensor-fusion-support-3d-orientation.html.

(56) References Cited

OTHER PUBLICATIONS

Grenet et al., "SpaceCoder: a Nanometric 3D Position Sensing Device," CSEM Scientific & Technical Report, 1 page, 2011.
Helen, L., et al. "Investigation of tissue bioimpedance using a macro-needle with a potential application in determination of needle-to-nerve proximity", Proceedings of the 8th International Conference on Sensing Technology, Sep. 2-4, 2014, pp. 376-380.
Inition. Virtual Botox: Haptic App Simulated Injecting the Real Thing. Retrieved from http://inition.co.uk/case-study/virtual-botox-haptic-app-simulates-injecting-real-thing.
Kalvøy, H., et al., "Detection of intraneural needle-placement with multiple frequency bioimpedance monitoring: a novel method", Journal of Clinical Monitoring and Computing, Apr. 2016, 30(2):185-192.
Madgwick, Sebastian O.H., "An efficient orientation filter for inertial and inertial/magnetic sensor arrays," 32 pp., Apr. 30, 2010.
Microsoft, "Integrating Motion and Orientation Sensors," 85 pp., Jun. 10, 2013.
Miller, Nathan L., Low-Power, Miniature Inertial Navigation System with Embedded GPS and Extended Kalman Filter, MicroStrain, Inc., 12 pp., 2012.
MPU-9150 9-Axis Evaluation Board User Guide, Revision 1.0, 15 pp., May 11, 2011, http//www.invensense.com.
MPU-9150, Register Map and Descriptions, Revision 4.2, 52 pp., Sep. 18, 2013, http//www.invensense.com.
MPU-9150, Product Specification, Revision 4.3, 50 pp., Sep. 18, 2013, http://www.invensense.com.
PST Iris Tracker, Plug and Play, 3D optical motion tracking specifications, 1 p., Dec. 4, 2014, www.pstech.com.
PST Iris Tracker, Instruction Manual, 3D optical motion tracking specifications, 42 pp., Jul. 27, 2012, www.pstech.com.
Struik, Pieter, "Ultra Low-Power 9D Fusion Implementation: A Case Study," Synopsis, Inc., 7 pp., Jun. 2014.
Sutherland, et al. "An Augmented Reality Haptic Training Simulator for Spinal Needle Procedures," IEEE, 2011.
Varesano, Fabio, "Prototyping Orientation and Motion Sensing Objects with Open Hardware," Dipartimento di Informatica, Univ. Torino, http://www.di.unito.it/~varesano, Feb. 10, 2013, 4 pp.
Varesano, Fabio, "FreeIMU: An Open Hardware Framework for Orientation and Motion Sensing," Dipartimento di Informatica, Univ. Torino, http://www.di.unito.it/~varesano, Mar. 20, 2013, 10 pp.
"A beginner's guide to accelerometers," Dimension Engineering LLC, accessed Jul. 11, 2018, in 2 pages, https://www.dimensionengineering.com/info/accelerometers.
"Accelerometer: Introduction to Acceleration Measurement," Omega Engineering, Sep. 17, 2015, 3 pages, https://www.omega.com/prodinfo/accelerometers.html.
"B-Smart disposable manometer for measuring peripheral nerve block injection pressures", Bbraun USA, 2016, in 4 pages.
Lee et al., "Augmented reality intravenous injection simulator based 3D medical imaging for veterinary medicine," The Veterinary Journal, 2013, vol. 196, No. 2, pp. 197-202.
"About the Journal", *J. Dental Educ., AM. Dental Educ. Ass'n*, 2019, http://www.jdentaled.org/content/about-us (last visited Oct. 9, 2019).
Begg et al., "Computational Intelligence for Movement Sciences: Neural Networks and Other Emerging Techniques", *IDEA Group Inc (IGI)*, 2006.
Comsa et al, "Bioluminescene imaging of point sources implants in small animals post mortem: evaluation of a method for estimating source strength and depth", *Phys. Med. Biol.*, Aug. 2007, vol. 52, No. 17, pp. 5415-5428.
Hotraphinyo et al., "Precision measurement for microsurgical instrument evaluation", *Conference Proceedings of the 23rd Annual International Conference of the IEEE Engineering in Medicine and Biology Societyl*, 2001, vol. 4, pp. 3454-3457.
Krupa et al., "Autonomous 3-D positioning of surgical instruments in robotized laparoscopic surgery using visual servoing", *IEEE Trans. Robotics and Automation*, 2003, vol. 19, pp. 842-853.
Liu et al. "Robust Real-Time Localization of Surgical Instruments in the Eye Surgery Stimulator (EyeSi)", *Signal and Image Processing*, 2002.
Merril et al., "The Ophthalmic Retrobulbar Injection Simulator (ORIS): An Application of Virtual Reality to Medical Education", *Proc. Ann. Symp. Comput. Med. Care*, 1992, pp. 702-706.
Mukherjee et al., "A Hall Effect Sensor Based Syringe Injection Rate Detector", *IEEE 2012 Sixth Int'l Conf. on Sensing Technol. (ICST)*, Dec. 18-21, 2012.
Patterson et al., "Absorption spectroscopy in tissue-simulating materials: a theoretical and experimental study of photon paths", Appl. Optics, Jan. 1995, vol. 34, No. 1, pp. 22-30.
Van Sickle et al., "Construct validation of the ProMIS simulator using novel laparoscopic suturing task", *Surg Endosc*, Sep. 2005, vol. 19, No. 9, pp. 1227-1231.
Wierinck et al., "Expert Performance on a Virtual Reality Simulation System", 71 *J. Dental Educ.*, Jun. 2007, pp. 759-766.
Wik et al., "Intubation with laryngoscope versus transillumination performed by paramedic students on mainkins and cadavers", *Resuscitation*, Jan. 1997, vol. 33, No. 3, pp. 215-218.

\* cited by examiner

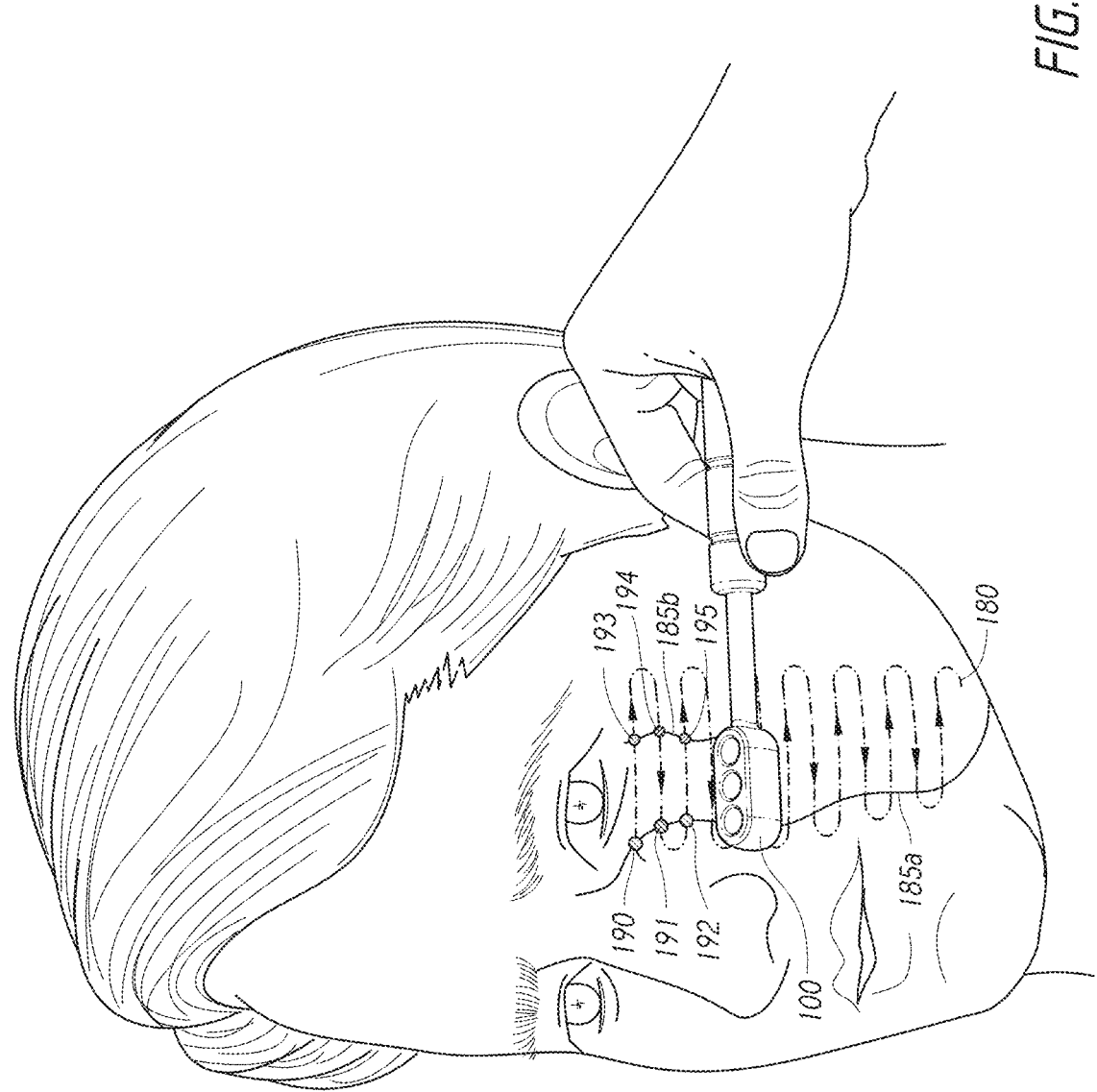

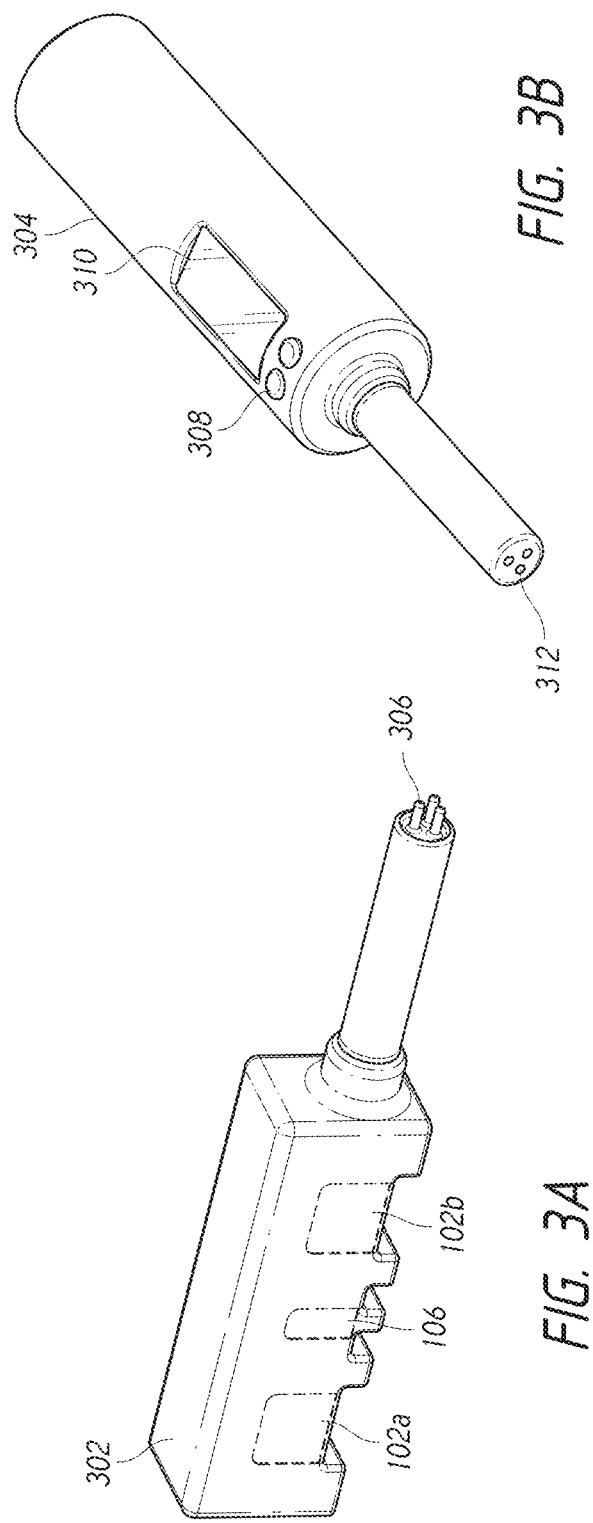

COSMETIC AND THERAPEUTIC INJECTION SAFETY SYSTEMS, METHODS, AND DEVICES

CROSS-REFERENCE TO RELATED APPLICATIONS

The present application claims priority benefit under 35 U.S.C. § 119(e) to U.S. Provisional Application No. 62/301462, filed Feb. 29, 2016, and U.S. Provisional Application No. 62/303251, filed Mar. 3, 2016, all of which applications are hereby incorporated by reference in their entirety herein.

FIELD OF THE DISCLOSURE

The present application relates generally to cosmetic and therapeutic injections, and more specifically to systems, devices, and methods for cosmetic and therapeutic injection safety.

BACKGROUND

A variety of medical injection procedures are often performed in prophylactic, curative, therapeutic, or cosmetic treatments. Injections may be administered in various locations on the body, such as under the conjunctiva, into arteries, bone marrow, the spine, the sternum, the pleural space of the chest region, the peritoneal cavity, joint spaces, and internal organs. Injections can also be helpful in administering medication directly into anatomic locations that are generating pain. These injections may be administered intravenously (through the vein), intramuscularly (into the muscle), intradermally (beneath the skin), subcutaneously (into the fatty layer of skin) or intraperitoneal injections (into the body cavity). Injections can be performed on humans as well as animals. The methods of administering injections typically range for different procedures and may depend on the substance being injected, needle size, or area of injection.

Injections are not limited to treating medical conditions, but may be expanded to treating aesthetic imperfections or restorative cosmetic procedures. Many of these procedures are performed through injections of various products into different parts of the body. The aesthetics and therapeutic industry consists of two main categories of injectable products: neuromodulators and dermal fillers. The neuromodulator industry commonly utilizes nerve-inhibiting products such as Botox®, Dysport®, and Xeomin®. The dermal filler industry utilizes products administered by providers to patients for both cosmetic and therapeutic reasons, such as, for example, Juvederm®, Restylane®, Belotero®, Sculptra®, Artefill®, and others. These providers or injectors may include plastic surgeons, facial plastic surgeons, oculoplastic surgeons, dermatologists, nurse practitioners, dentists, and nurses.

Given the variety of injectable products and subjects into which the products will be injected, it is desirable to provide injection safety systems, methods, and devices that reduce error in delivering not only those products available today but also those yet to be deployed.

SUMMARY

When using a needle-based device, for example a syringe for therapeutic injections, there is a risk of puncturing a blood vessel or hitting a nerve with the needle. Further, it can be difficult to assess that the needle tip is located in correct layer of tissue, which may impact, for example, patient safety, the effectiveness of a blood draw, the performance of an injectable therapeutic. Imaging modalities, such as x-ray, CT, MRI, or the like, can be used prior to a procedure to understand the anatomy surrounding an injection site, these procedures can be expensive, time-consuming, and require analysis. Further, these imaging modalities cannot be used to determine a real-time location of a distal tip of a needle. Thus, there is a need for a medical device that can provide a real-time indication of a location of the distal tip of the needle in living tissue. Such a medical device would enable a clinician to perform the procedure quickly and accurately in an out-patient setting such as a physician's office or even developing areas where the above-described imaging modalities are not available. Further, a guided medical device could be integrated into a robotic system, which could limit, modify, guide, and/or halt movement of the medical device based on the indications provided by the features described herein.

Some aspects of the disclosure are directed toward a system that can determine whether a distal tip of a medical device (e.g., a needle-based device) is in a blood vessel. The medical device can include a sensor for detecting motion, pressure, and/or vibration at the distal tip of the medical device. The sensor can generate a signal based on the detected motion, pressure, and/or vibration. The system can also include a processing unit configured to perform a process that provides an indication of whether the distal tip of the medical device is in the blood vessel by comparing an aspect (e.g., frequency, amplitude, or otherwise) of the generated signal to a threshold value.

Some aspects of the disclosure are directed toward a system for determining a proximity of a medical device (e.g., a needle-based device) to a nerve. The system can include a pulse generator, a detector, and a processing unit. The pulse generator can be configured to supply an electrical current to a distal tip of the medical device. The detector can be configured to detect a physiological response to the electrical current and generate a signal. The processing unit can be configured to perform a process that provides an indication representative of the proximity of the distal tip of the medical device to a nerve based on the comparison between the generated signal and the threshold value.

Some aspects of the disclosure are directed toward a system for determining a depth of insertion for a medical device (e.g., a needle-based device). The system can include a pulse generator and a vibration sensor. The pulse generator can be configured to supply a pulse (e.g., mechanical or electrical) to a patient's skin at a first time mark. The vibration sensor can be configured to detect a first vibration of the needle in response to the generated pulse at a second time mark. The system can also include a processing unit configured to perform a process that determines a distance between the patient's skin and a distal tip of the needle based on a first time delay between the first time mark and the second time mark. In some implementations, the vibration sensor can be configured to detect a second vibration of the needle at a third time mark. The process can determine a distance between the distal tip of the needle and a bone based on a second time delay between the second time mark and the third time mark.

Some aspects of the disclosure are directed toward displaying the physiological features detected by the various systems disclosed herein.

For example, the physiological features may be displayed using an augmented or virtual reality system. The system can include a computing system having at least one processor and a memory device. The computing system can be configured to generate a virtual environment comprising a graphical representation at least one layer of tissue of a patient (e.g., muscles, nerves, bones, and/or vessels). A display device coupled to the computing system can be configured to mesh the virtual environment on the patient, such that a location in the virtual environment is aligned with a same location in the patient.

As another example, the physiological features may be displayed by a physiological mapping device. The device includes a sensor configured to detect a physiological feature beneath a skin surface of a subject using any of the systems and methods disclosed herein. The device also includes an information processor configured to receive information from the sensor indicative of the physiological feature and identify the physiological feature based on the received emissions. The device further includes a marking element configured to produce a visible mark on the skin surface identifying the physiological feature based on the received identification.

In some implementations, the sensor may include one of a piezoelectric sensor, a microphone, an antenna, a gyroscope, or an accelerometer. The physiological feature may include one of a vein, an artery, or a nerve. In some implementations, the information processor is further configured to determine a depth of the identified physiological feature beneath the surface. In such implementations, the marking element is further configured to produce the visible mark to further identify the depth.

Some devices may include an emitter. In these devices, a detector detects a reflected portion of a signal transmitted by the emitter, and the information processor is configured to identify the physiological feature based on a comparison of the signal transmitted by the emitter and the detected signal.

The sensor and the marking element may be formed in a head while the information processor may be formed in a base. In such implementations, the head is detachable from the base.

In a further innovative aspect, a physiological mapping device head is provided. The head includes a sensor configured to detect a physiological feature beneath a surface of a subject. The head also includes a coupling configured to transmit detected information to an information processor and receive physiological information from the information processor. The head further includes a marking element configured to receive an identification of the physiological feature from an information processor via the coupling and produce a visible mark on the surface identifying the physiological feature based on the received identification.

In yet another innovative aspect, a physiological mapping device body is provided. The body includes a coupling configured to exchange data with a head that includes a sensor and a marking element. The body includes an information processor which is configured to detect a physiological feature beneath a surface of a subject from the sensor and transmit an identification of the physiological feature to the marking element. The identification includes information causing, in part, the production of a visible mark on the surface identifying the physiological feature.

A nerve safe needle is provided in yet another innovative aspect. The needle includes a tip formed of an electrically conductive material. The needle also includes a power source coupled with the tip. Upon contact of the tip with a nerve, a circuit is completed with the tip and the power source to deliver a current at the tip. The circuit may be configured to deliver a current sufficient to cause a physiological response.

An aspirating needle is provided in another innovative aspect. The needle includes a hollow needle tip coupled with a chamber. The chamber includes a first channel to an injectable reservoir and a second channel to an aspirator reservoir. The aspirator reservoir includes an oscillating member configured to oscillate a fluid between the aspirator reservoir to the hollow needle tip. The aspirator reservoir also includes a light source affixed on a wall of the aspirator reservoir and configured to emit light of a predetermined quality. The aspirator reservoir further includes a light detector affixed on the wall of the aspirator reservoir opposite the light source such that a center point of the light source is aligned with a center point of the light detector. The light detector is configured to detect a characteristic of the light emitted from the light source through the fluid in the aspirator reservoir.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

The systems, methods, devices, and computer program products discussed herein each have several aspects, no single one of which is solely responsible for its desirable attributes. Without limiting the scope of this invention as expressed by the claims which follow, some features are discussed briefly below. After considering this discussion, and particularly after reading the section entitled "Detailed Description," it will be understood how advantageous features of this invention include, among other things, injection safety.

One of the major problems in the administration of injections is accurate delivery of the injectable to the injection site. Not only is the location important, but also the quantity injected is important for safe and effective use of these substances. Described in further detail below are aspects of systems, methods, and devices for enhancing the safety and effectiveness of injections.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIG. 1 shows an exemplary scanning printer during a mapping session.

FIGS. 3A and 3B show illustrations of an example of an injection scanning printer including a head and a base.

DETAILED DESCRIPTION

The present disclosure generally relates to injection safety systems, methods, and devices.

Mapping Systems

One feature which provides improved safety is to identify the location of critical physiological features before injecting. For example, some injectables are designed for subcutaneous injection. Delivering such injectables into a physiological feature such as a vein or artery can cause serious side effects. For example, injecting filler into a vein or artery of a human subject may block blood flow thereby killing local tissue or optical nerves. In some extreme cases, these blockages can cause blindness.

Accordingly, having a "map" of the subject's physiology before injecting would reduce the likelihood of injecting into a critical area. It is important to note that each subject's physiology is different. As such, the location of features may differ from subject to subject. In addition, the proximity of the features to the skin (e.g., depth) may also differ between subjects. To generate the map, the present disclosure provides a device that detects the presence of a physiological feature and provides a visual indication of the feature. Although some embodiments might describe a single device that detects both the presence of a physiological feature and provides a visual indication of the feature, it is contemplated that a device might only perform one of these functions. It is further contemplated that a system might include a first device for detecting the presence of a physiological feature using any of the methods described herein, and a second device for providing a visual indication of the physiological feature using any of the methods described herein (e.g., a scanning printer, augmented reality system, or a virtual reality system).

FIG. 1 shows an exemplary scanning printer during a mapping session. The scanning printer 100 is cast over a portion of a subject via a path 180. In FIG. 1, the subject is a human face. As the scanning printer 100 detects physiological features such as veins or arteries (shown as 185a and 185b), the scanning printer 100 causes the printing of marks 190 through 195 on the surface of the subject. This provides a visible indication of where potentially sensitive features exist to improve the safety of the injection process. The marks may also be different depending on the underlying feature. As shown in FIG. 1, marks 190 through 192 are larger than the marks 193 through 195. The size may be used to indicate different features and/or different depth of the features as described in further detail below. The scanning printer 100 as shown in FIG. 1 is implemented as a facial scanner/printer, included, for example, in a wand or handheld housing. It will be appreciated that the scanning printer 100 may be implemented in a different form factor other than a wand and for scanning surfaces other than a human face.

Figure 2A:
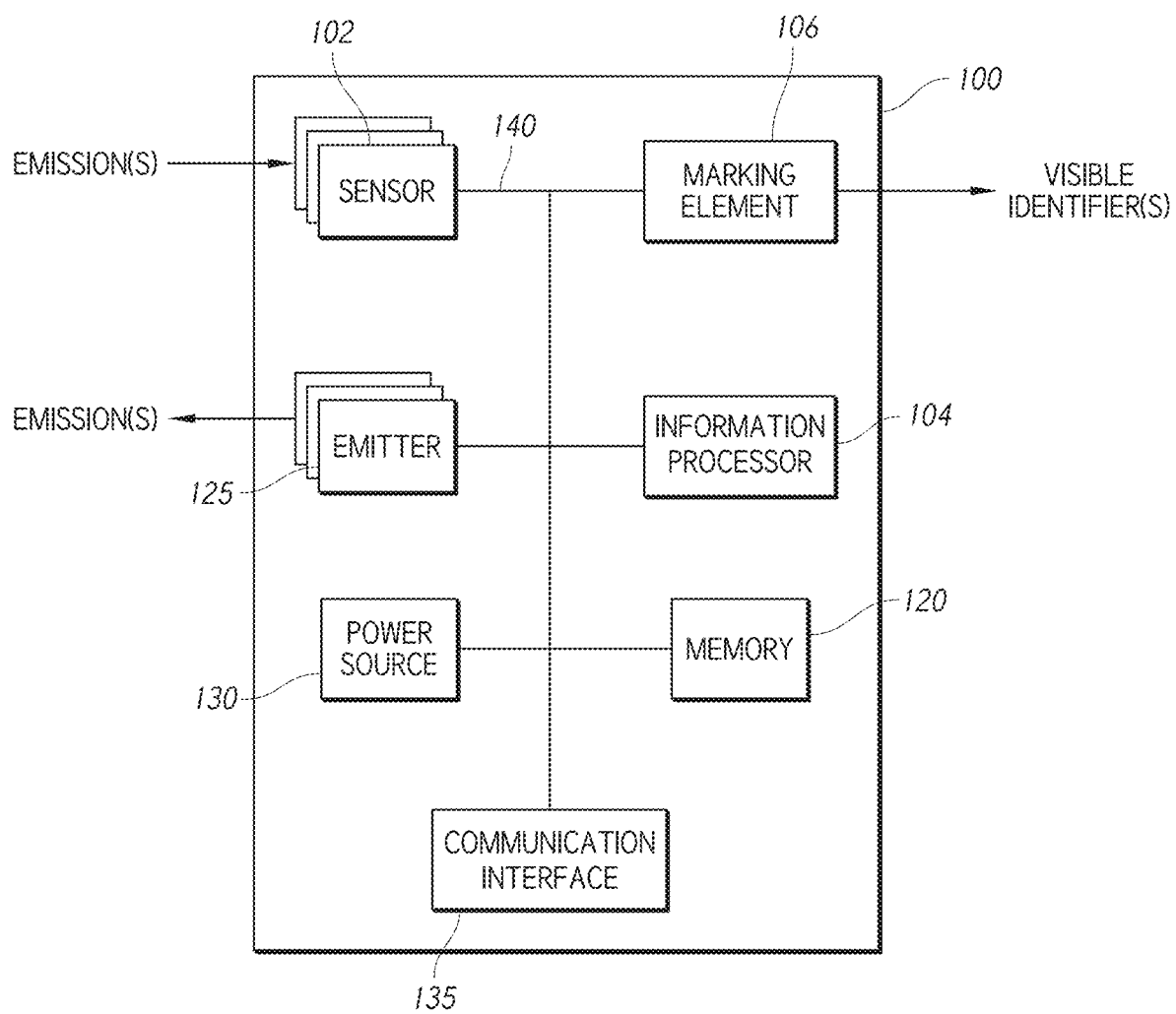
FIG. 2A shows a functional block diagram of an exemplary injection scanning printer.

FIG. 2A shows a functional block diagram of an exemplary injection scanning printer. The scanning printer 100 includes one or more sensors 102. The sensors 102 are configured to detect emissions from a physiological feature. The sensors 102 can be configured to detect the physiological features using any of the methods described herein, including those systems shown in FIGS. 10-16. For example, the sensors 102 may be implemented as a microphone and configured to detect sound emitted from the physiological feature. The sensors 102 may be implemented as an antenna and configured to detect electrical activity from the physiological feature. The sensors 102 may be implemented as an accelerometer and configured to detect motion caused by, for example, pulsing of the physiological feature. The sensors 102 may be configured to detect the information over a period of time thus providing a sampling for an area. The sensors 102 may be implemented as a piezoelectric sensor configured to detect vibrations from the physiological feature. It will be appreciated that in some implementations, multiple sensors may be included in the scanning printer 100 and each sensor may be the same or of a different type. It will be further appreciated that in some implementations, only one sensor may be included in the scanning printer 100.

The sensor 102 is coupled with an information processor 104. The information processor 104 is configured to receive the information detected by the sensor 102. The information processor 104 may compare the detected information with physiological "signatures" stored in a memory 120. For example, an artery may emit sound at a certain volume and/or frequency. By comparing the received volume or frequency information to previously determined volume or frequency information for an artery, the information processor 104 may identify the artery.

The information processor 104 may be configured to determined not just the location of the physiological feature, but also the depth of the feature beneath the surface (e.g., under the skin). The depth may be determined based on the information received from the sensor 102. In some implementations, the frequency may be used to identify the feature while the volume is used to determine the depth.

Figure 2B:
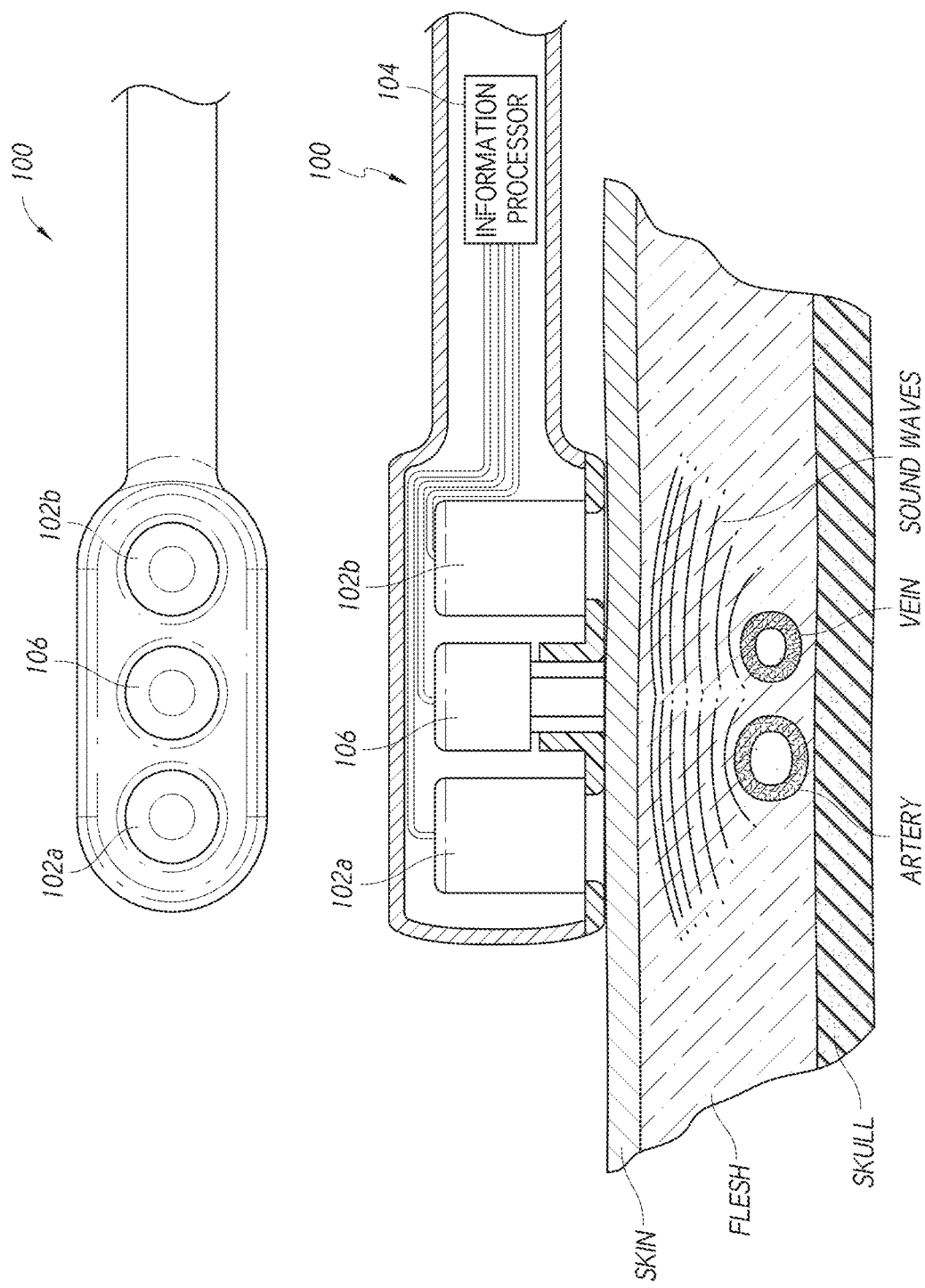
FIG. 2B shows an operational diagram of an implementation of an injection scanning printer.

In some implementations, the scanning printer 100 may include one or more emitters 125 (shown in FIG. 2A but not shown in FIG. 2B). In such implementations, the sensor 102 may be configured to detect a quantity of an emission after the emitter 125 transmits the emission. The emission and detection may be coordinated by the information processor 104. A comparison of the emitted information to the detected information can be used to determine the location and depth of a physiological feature as described herein.

The information processor 104, upon identifying a physiological feature, may be configured to transmit a message to a marking element 106. The marking element 106 is configured to provide one or more visible identifiers on the surface of the subject identifying the detected physiological feature. The message may identify the type of mark to make. For example, arteries may be identified with a predetermined symbol or color while veins may be identified with a different symbol or color. The message may identify the size of the mark to make whereby the closer the feature is to the surface of the subject, the larger the mark will be. Of course, other marking systems can be used to provide an indication of depth. In some embodiments, the visible identifiers are directly applied to the patient's skin. For example, the marking element 106 may be an ink marking element. In some implementations, the marking element 106 may be actuated such that an ink containing portion is lowered to contact the surface of the subject to produce the visible mark. In some implementations, the marking element 106 may include a pump configured to spray a marking fluid (e.g., ink) onto the surface of the subject to produce the visible mark. In other embodiments, the visual identifiers may not be physically applied to the skin, for example, the marking element 106 might simply output an image of the physiological features or other light-based indicators.

In some implementations, the scanning printer 100 may include means for providing the location of the scanning printer 100. For example, the scanning printer 100 may be configured prior to mapping by placing the scanning printer 100 at one or more known features such as corner of an eye, tip of nose, or other landmark. The means for providing the location of the scanning printer 100 may then be configured to provide a relative location of the scanning printer 100 to the known features. This additional location information may be used by the information processor 104 to further identify the physiological features. The means for providing the location of the scanning printer 100 may include one or more of: an accelerometer, a gyroscope, and a positioning receiver.

The scanning printer 100 may include a communication interface 135 configured to transmit and receive information. The communication interface 135 may be configured to receive physiological signature data for use by the information processor 104. For example, if a user of the scanning printer 100 is going to inject an animal with a muscle relaxer, the signature data for the animal and injectable substance may be transferred to the scanning printer 100 via the communication interface 135 and stored in the memory 120. Accordingly, the scanning printer 100 can be dynamically reconfigured for detecting a variety of physiological features. The communication interface 135 may be configured for communication via Bluetooth™, Universal Serial Bus, cellular networks, WiFi™ networks, near field communication, or other standardized communication protocol.

The scanning printer 100 shown in FIG. 2A includes a power source 130. The power source 130 may be a battery, a cord, or other means for powering the scanning printer 100. The elements of the scanning printer 100 are coupled by a bus 140. The bus 140 is configured to allow the elements to exchange data and/or power. In some implementations, parallel busses may be included, one for data and one for power.

FIG. 2B shows an operational diagram of an implementation of an injection scanning printer. The scanning printer 100 shown in FIG. 2B includes two sensors configured to detect information emitted by the physiological feature, sensor 102a and sensor 102b (collectively and individually hereinafter referred to as "sensors 102"). The sensors 102 are configured in a housing on either side of the marking element 106. The sensors 102 and the marking element 106 are coupled with the information process 104 to allow data communication between the elements.

The sensors 102 can detect sound waves from physiological features such as veins or arteries as they travel through the flesh and skin of a subject. While FIG. 2B shows the location of the mapping as a skull, it will be appreciated that the scanning printer 100 may be configured for mapping other parts of the body (e.g., spine, neck, leg, arm, or hand) as well as non-human subjects such as dogs or iguanas.

In some implementations, the sensor 102 and marking element 106 may be included in a head which can be coupled with a base. FIG. 3A and FIG. 3B show illustrations of an example of an injection scanning printer including a head and a base. FIG. 3A shows the head 302 while FIG. 3B shows the base 304. This configuration allows the head 302 of the scanning printer 100 to be disposed of after a use while the base 304 may be reused. The head 302 may be referred to as a "one time use head" or a "per subject use head." In such implementations, the base 304 may include a power source such as a battery. When the head 302 couples with the base 304, power may be delivered to the marking element 106 and the sensor 102. The coupling also creates a pathway for the information exchanges between the sensor 102 and/or marking element 106 and the information processor 104 described above. In implementations which include an emitter, the emitter may be included in the head 302 as well. In such implementations, additional data and/or power pathways may be included to couple the emitter with the information processor 104 and/or the power source 130 which may be included in the base 304. As shown in FIG. 3A and FIG. 3B, three pins 306 are used to couple the head 302 to the base 304 which includes corresponding ports 312. It will be appreciated that fewer or more pins may be used to couple the head 302 to the base 304. The number of pins may be based in part on the number of pathways (e.g., data and power) needed for the scanning printer 100 configuration.

The base 304 may include the communication interface 135 (not shown) to transmit and receive information. In some implementations, the communication interface 135 may be located within the base 304 housing. For example, if the communication interface 135 provides wireless communications, the antenna, transceiver, and other elements may be included within the base 304. In some implementations, the communication interface 135 may include a connection port for wired communications such as USB or serial communication. In such implementations, the base 304 may include a port (not shown) configured to receive a wired connection. As discussed above, the communication interface 135 may be configured to receive physiological signature data for use by the information processor 104. Accordingly, the same base 304 can be reconfigured for detecting a variety of physiological features. Furthermore, the same base 304 may be configured to map using different head configurations. For example, when mapping a leg, it may be desirable to use a head including a single microphone as the sensor. However, when mapping a spine, it may be desirable to use a head which includes multiple sensors of higher sensitivity. Accordingly, the same base 304 may be dynamically reconfigured to process the information detected from a variety of head configurations.

In some implementations, the base 304 may include a reservoir (not shown). The reservoir may be configured to hold a marking fluid for use by the marking element 106. In such implementations, an additional marking fluid pathway (e.g., duct) may be included to enable delivery of the marking fluid from the base 304 to the marking element 106. In some implementations, the marking fluid may be stored in the head 302.

The base 304 may, in some implementation, include a light 308 and/or a display 310 configured to provide feedback to a user. For example, the light 308 may illuminate green when a physiological feature is detected. The display 310 may be used for calibrating the location of the scanning printer 100 or providing feedback to the user about the scanning printer 100 usage. For example, the user may be moving the scanning printer 100 too quickly to obtain a reading. In such situations, the information processor 104 may be configured to provide a message for displaying on the display 310 indicating a rescan is needed. The display 310 may be configured to provide feedback regarding the marking fluid level. The display 310 may also be configured to provide feedback regarding the signature data stored in the memory and information port connectivity status. For example, the scanning printer 100 may exchange information via Bluetooth™. Once paired, the display 310 may be configured to display the Bluetooth™ symbol. The display 310 may also be configured to provide an indication of the available power (e.g., battery level) for the scanning printer 100.

In some implementations, the head 302 and the base 304 may be permanently coupled. In such implementations, it may be desirable to provide a low cost scanning printer such that the entire device may be disposable. In some implementations, the cost of the sensor or other components may result in a design which is reusable. In such reusable designs, the resources used by the scanning printer (e.g., marking fluid, power) are configured for replenishment. For example, the marking fluid reservoir may be refilled such as via a refill pinhole. Power may be replenished through the use of a rechargeable or swappable battery.

Another safety innovation relates to the needle. As described above, delivering filler to sensitive areas can have serious consequences. Therefore, configuring the needle to determine what it piercing provides information regarding where the filler will be delivered before actually injecting the filler. For example, the needle tip may be inserted through the skin toward a target area. During placement or once in place, the needle may provide an indication as to whether it is in contact with a nerve. The subject is electrically grounded. The needle may be configured to provide an electrical charge. As configured, if the needle is near a nerve, the electrical charge will cause a physical reaction such as a sensation or twitching. By provoking the body to provide a reaction, the subject and the user of the injector may be alerted to potentially dangerous placement of the needle.

Figure 4A:
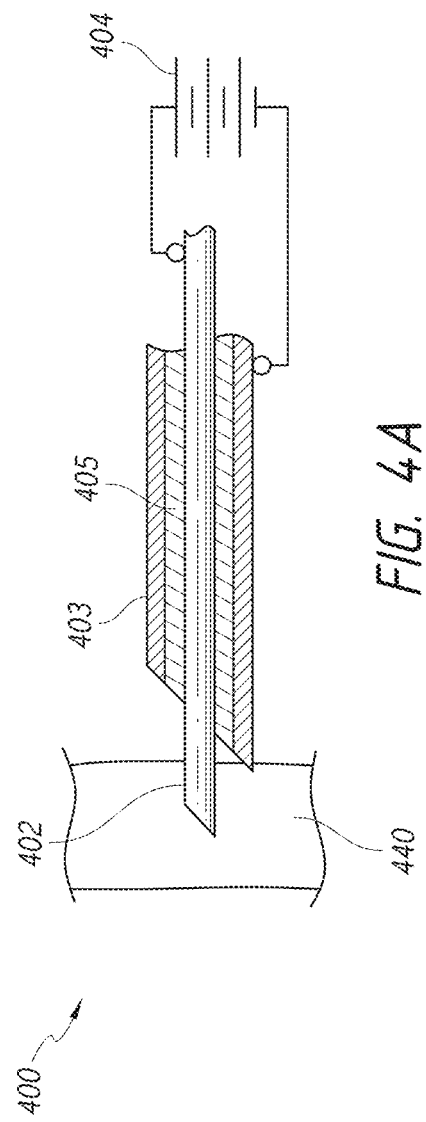
FIG. 4A shows a cross-sectional view of an exemplary nerve detecting needle.

FIG. 4A shows a cross-sectional view of an exemplary nerve detecting needle. The nerve detecting needle 400 includes a tip 402. The tip 402 is formed of an electrically conductive material such as stainless steel. The tip 402 is connected to a power source 404. An electrically conductive sleeve 403 is separated from the tip 402 by an electrical insulation layer 405. The electrically conductive sleeve 403 may be formed of an electrically conductive material such as stainless steel although the conductive material forming the sleeve 403 need not be the same material as used for the tip 402. The electrical insulation layer 405 may be formed of material which inhibits the flow of electric such as fluoropolymers, rubber-like polymers, or plastics.

The conductive sleeve 403 is connected to the power source 404. Although not shown, additional components such as transistors or capacitors may be coupled between one or more of the power source 404, the conductive sleeve 403, and the tip 402 to regulate the flow and quantity of power discharged when a nerve is touched. In some implementations, a feedback element such as an audio alert, a visual alert (e.g., light), or haptic (e.g., vibration) may be included whereby the detection causes activation of the feedback element thus alerting a user to the location of a nerve.

Figure 4B:
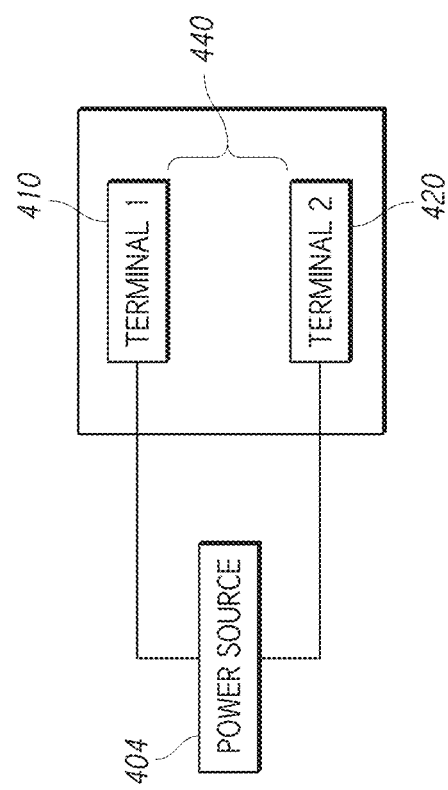
FIG. 4B shows a functional block diagram of an exemplary nerve detecting needle.

FIG. 4B shows a functional block diagram of an exemplary nerve detecting needle. The power source 404 is coupled with a first terminal 410. The first terminal 410 is located at the tip 402 of the needle. Separated from the first terminal 410 is a second terminal 420. The second terminal 420 is then coupled with the power source 404 and the conductive sleeve 403. The space between the first terminal 410 and the second terminal 420 creates a nerve detection zone 440. In some implementations, it may be desirable to include a nerve detection zone 440 having a width of 0.5 to 2.0 millimeters between the first terminal 410 and the second terminal 420. When a conductive element enters the nerve detection zone 440, the circuit is completed and a current will flow. The circuit is configured such that the current will cause a physical reaction such as a sensation or twitching in the subject. By provoking the body to provide a reaction, the subject and the user of the injector may be alerted to potentially dangerous placement of the needle. Although not shown, additional components such as transistors or capacitors may be coupled between the power source 404, the first terminal 410, and/or the second terminal 420 to regulate the flow and quantity of power discharged when a nerve is touched.

A further safety innovation relating to the needle provides detection of an artery or vein based on aspirating blood. The needle may be configured for auto aspiration. A reservoir would be configured such that blood in a vein or artery could be aspirated from the vein or artery through the needle tip into a saline reservoir. A sensor such as an optical detector may be configured to monitor the reservoir. Absent blood in the reservoir, the saline reservoir exhibits a neutral optical spectrum. The sensor may detect a change from neutral to red as blood enters the reservoir. The redness serves as an indication that the needle has pierced a vein or artery. Although discussed in terms of aspiration of blood, the describe features may be applied to provide detection of other intra or extra cellular fluids that may be found in or around an injection site.

Figure 5:
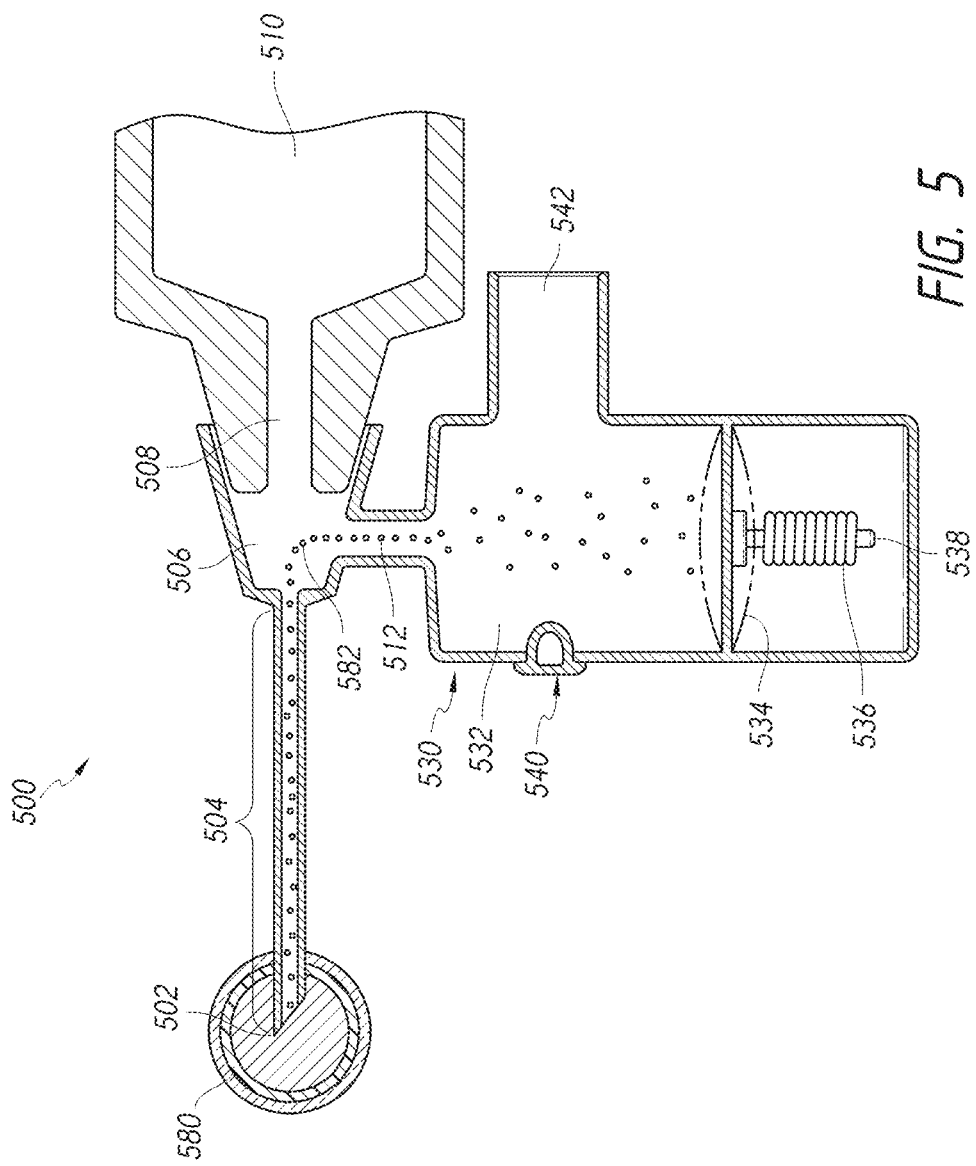
FIG. 5 shows a cross-sectional view of an exemplary aspirating safety needle.

FIG. 5 shows a cross-sectional view of an exemplary aspirating safety needle. The needle 500 includes a tip 502. The tip 502 includes a hollow channel 504 which is coupled with a forward chamber 506. The forward chamber 506 includes two channels. A first channel 508 leads to a filler reservoir 510. The filler reservoir 510 is configured to hold the injectable filler. A second channel 512 leads to an aspirator reservoir 530. The aspirator reservoir 530 includes fluid reservoir 532. At the base of the fluid reservoir 532 an oscillating member 534 is affixed. The oscillating member 534 is configured with a displacement greater than twice the combined volumes of the hollow channel 504, the forward chamber 506, and the second channel 512. The oscillating member 534 may include a coil 536 and a magnet 538 configured to actuate the oscillating member 534 at a predetermined frequency. In some implementations, the frequency may be between 1 and 5 hertz. The motion of the oscillating member 534 causes the fluid within the fluid reservoir 532 to circulate from the aspirator reservoir 530 through the second channel 512 through the forward chamber 506 and to the tip 502 and back into the aspirator reservoir 530. This allows any blood contacted at the tip 502 to be circulated back into the aspirator reservoir 530. As shown in FIG. 5, a vessel 580 is pierced by the tip 502 which causes a stream of droplets 582 to flow into the aspirator reservoir 530.

The aspirator reservoir 530 also includes a light source 540. The light source 540 may be a light emitting diode, a bulb, a laser, or other similar emitter. In some implementations, the light source 540 is a white light source. The light source 540 is affixed such that light can shine into the fluid reservoir 532. On an opposite side of the fluid reservoir 532, a light detector 542 is affixed such that a central point of the light detector 542 is aligned with a central point of the light source 540. The light detector 542 is configured to detect the color of the light as it passes through the fluid reservoir 532. The light detector 542 may transmit a message upon detecting light of a predetermined color such as red.

A power source (not shown) may be included to provide power for the oscillating member, coil, magnet, light source, and light detector. In some implementations, the needle 500 includes a processor (not shown). The processor may be configured to receive messages from the light detector and generate an indication once a color change is detected. The indication may include a sound, a haptic indication (e.g., vibration), a visual indication (e.g., light or display message), or combination thereof.

It will be appreciated that the needle 500 shown in FIG. 5 may include additional elements. For example needles or syringes typically include a plunger, which has been omitted in FIG. 5 to focus the reader on certain innovative safety aspects. Furthermore, although described as a separate innovative aspect, features of the aspirating safety needle may be combined with the nerve detecting needle 400 (and vice-versa) to provide multiple layers of safety during cosmetic or therapeutic injections.

Figure 6:
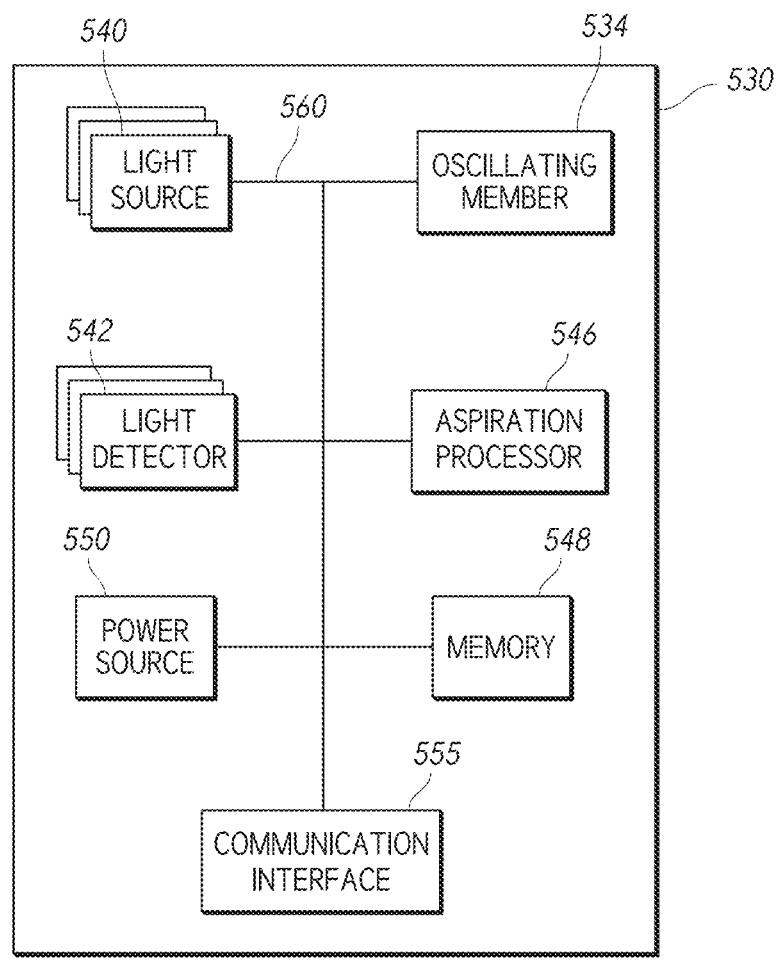
FIG. 6 shows a functional block diagram of an exemplary aspirator reservoir.

FIG. 6 shows a functional block diagram of an exemplary aspirator reservoir. The aspirator reservoir 530 shown in FIG. 6 highlights the interconnectivity of the elements which may be included in an implementation. The aspirator reservoir 530 includes one or more light sources 540. In implementations including multiple light sources, it may be desirable to affix the light sources 540 in a pattern opposite the light detector 542 to maximize the illumination of the reservoir fluid. The aspirator reservoir 530 may include one or more light detectors 542. In implementations where multiple light detectors are included, it may be desirable to arrange the detectors in a pattern to ensure sensing over a maximized area of reservoir fluid. In some implementations, where the number of sensors is equal to the number of detectors, it may be desirable to pair a sensor with a detector and align the centers of each. The light sources may be the same type of light (e.g., white) or have different characteristics. In such implementations, it may be desirable to create detection zones for each light type using different sensors.

An aspiration processor 546 may be configured to control the oscillating member 534, the light source 540, and the light detector 542. For example, it may be desirable to coordinate the cycle of oscillation, illumination, and detection so as to conserve power. In such implementations, a period of illumination may occur after an oscillation followed by a moment of detection. The aspiration processor 546 may also be configured to determine when a characteristic of the light detected indicates the presence of blood or other identifiable fluid. A memory 548 may be configured to store the light characteristics and response messages associated with detection thereof. The aspiration processor 546 compares the detected information with the stored characteristics to determine whether an identified fluid has been introduced into the aspirator reservoir 530. A communication interface 555 may be included to transmit and receive information to and from the aspirator reservoir 530. For example, upon detecting the introduction of a fluid into the reservoir, the communication interface 555 may transmit a message indicating the presence of a fluid. This may include an audio sound, a visual message, or a data message via a communication protocol such as Bluetooth™, near field communication, or other wireless protocol. The communication interface 555 may also be configured to receive characteristic information for identifiable fluids. The characteristics may be stored in the memory 548 for use by the aspiration processor 546. The communication interface 555 may receive operational parameters for the aspirating reservoir 530 such as an oscillation rate, lighting patterns, and detection patterns. The operational parameters may be stored in the memory 548 and used by the aspiration processor 546 in coordinating the functions of the aspirating reservoir 530 described above.

A power source 550 may be included to provide power for the elements of the aspirating reservoir 530. It may be desirable to include a small form factor power source due to the precision size of the needle. In such implementations, the power source 550 may be a coin cell. The elements of the aspirating reservoir 530 shown in FIG. 6 are coupled by a bus 560. The bus 560 is configured to allow the elements to exchange data and/or power. In some implementations, parallel busses may be included, such as one bus for data and one bus for power.

Figure 7:
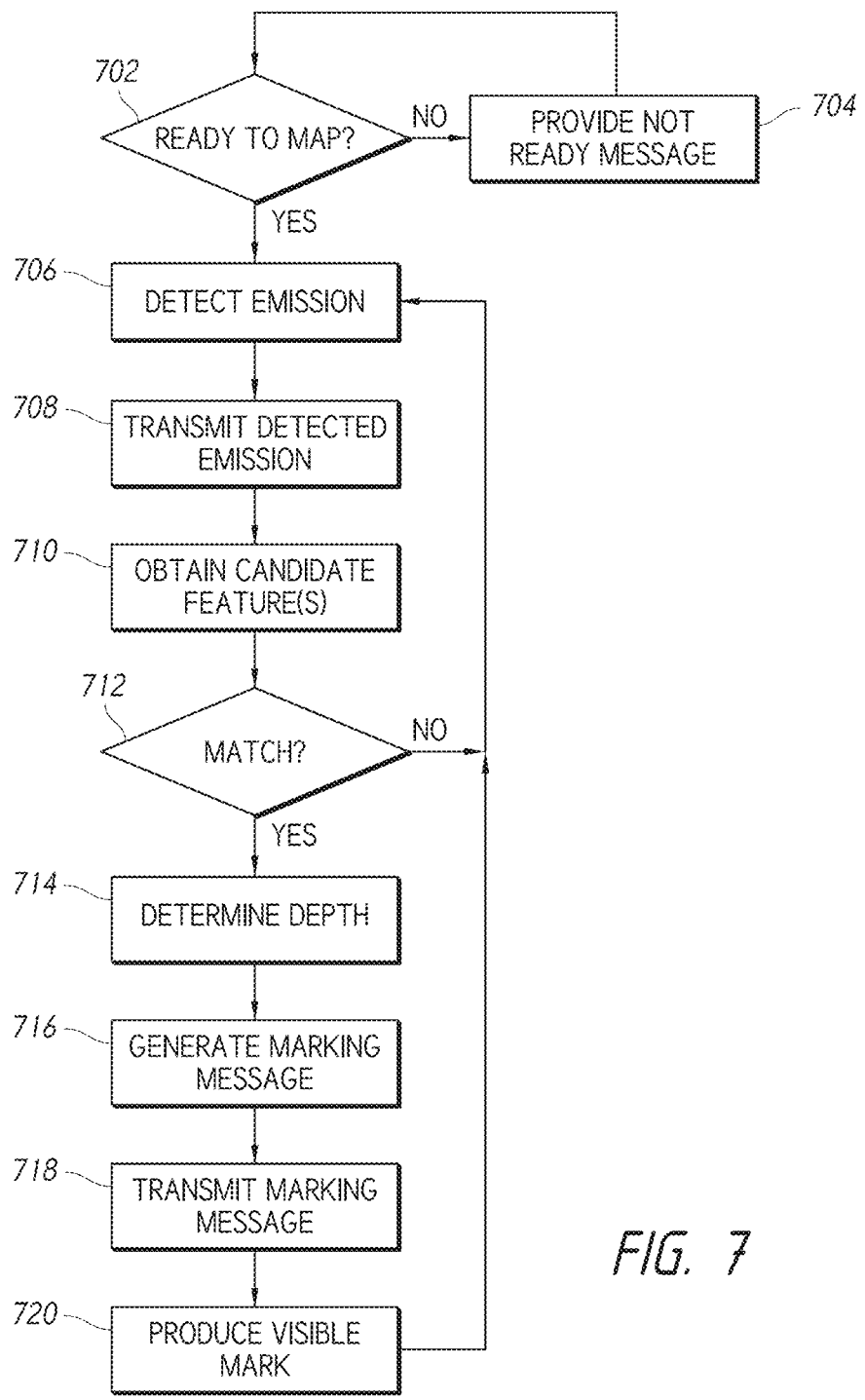
FIG. 7 illustrates a process flow diagram of a method of injection mapping.

FIG. 7 illustrates a process flow diagram of a method of injection mapping. The method of injection mapping shown in FIG. 7 may be implemented in part by the scanning printer 100 described above. As described above, although some embodiments might describe a single method that detects both the presence of a physiological feature and provides a visual indication of the feature, it is contemplated that the method might only carry out one of these functions.

The method begins at determination block 702 where a determination is made as to whether the device is ready to map. The determination may be based on sensor information. In some implementations, the scanning printer may include a contact detector which determined whether the wand is in contact with a surface (e.g., skin). If the determination at block 702 is negative, at block 704, a not ready message is provided. For example, a display may be provided a message identifying the scanning printer is not ready for mapping.

Returning to block 702, if the determination is made that the device is ready for mapping, at block 706, an emission is detected. The emission may be, for example, a sound wave from a physiological feature located beneath the surface being mapped. At block 708, the detected emission is transmitted from the sensor to the information processor. At block 710, the information processor obtains the candidate physiological features such as from a memory. The candidate features includes emission signatures for each feature. At decision block 712, a determination is made as to whether the received emission matches any of the emissions signatures. If not, the process returns to block 706 to continue detection. If a match is found, at block 714, the information processor may optionally determine the depth of the feature. The depth determination may be based on the received emission and the emission signature information. At block 716, a marking message is generated based on the matched feature and, if available, depth. At block 718, the marking message is transmitted to the marking element. At block 720, the marking element produces a visible mark based on the marking message on the surface of the subject. The visible mark identifies at least the location of a physiological feature. In some implementations, different marks may be made to identify the type of feature. In some implementations, the marks may be varied to indicate the relative depth of the feature. Once marked, the process may return to block 706 to continue detecting additional emissions and provide further mapping.

Figure 8:
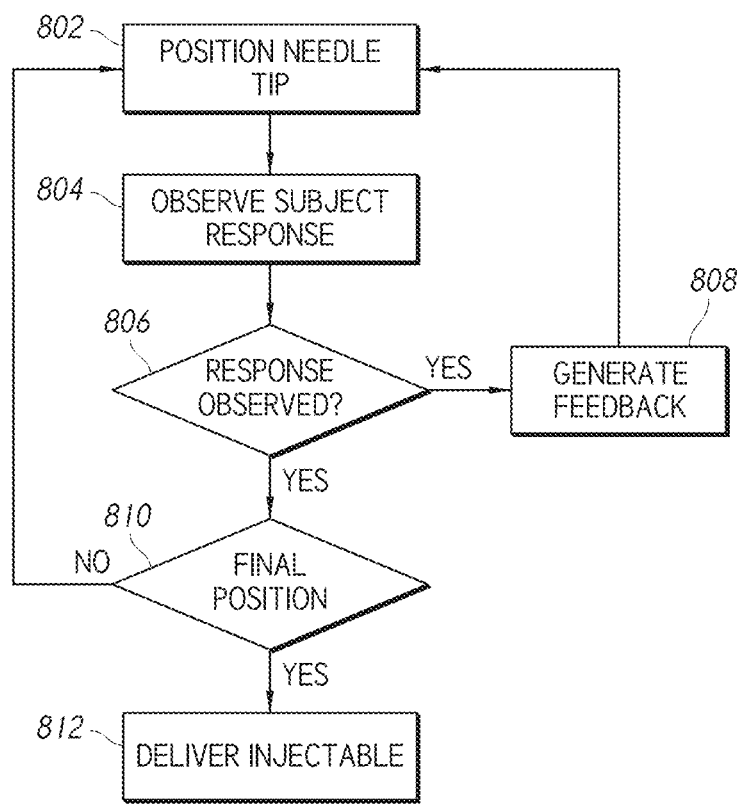
FIG. 8 illustrates a process flow diagram of a method of injecting with nerve safety.

FIG. 8 illustrates a process flow diagram of a method of injecting with nerve safety. The method may be implemented in part by the nerve detecting needle 400 described above. At block 802, the needle tip is positioned in the subject. At block 804, the subject is observed. In some implementations, the observation may be visual. In some implementations, a motion detector may be included to observe a response by the subject to the current needle position. At decision block 806, it is determined whether a response is observed. The response may be a twitching of the subject or a sensation (e.g., pain or heat) by the subject. If a response is observed, at block 808 feedback is generated. The feedback alerts the needle operator that a nerve may be contacted. Based on this feedback, the process may return to block 802 for further needle positioning. If a response is not observed at block 806, the process continues to determination block 810. At block 810, a determination is made as to whether the needle is in its final position. A final position generally refers to the position at which the injectable substance will be delivered. If it is determined at block 810 that the needle is not in its final position, the process returns to block 802 for further needle positioning. If it is determined at block 810 that the needle is in its final position, at block 812 the injectable substance is delivered.

Figure 9:
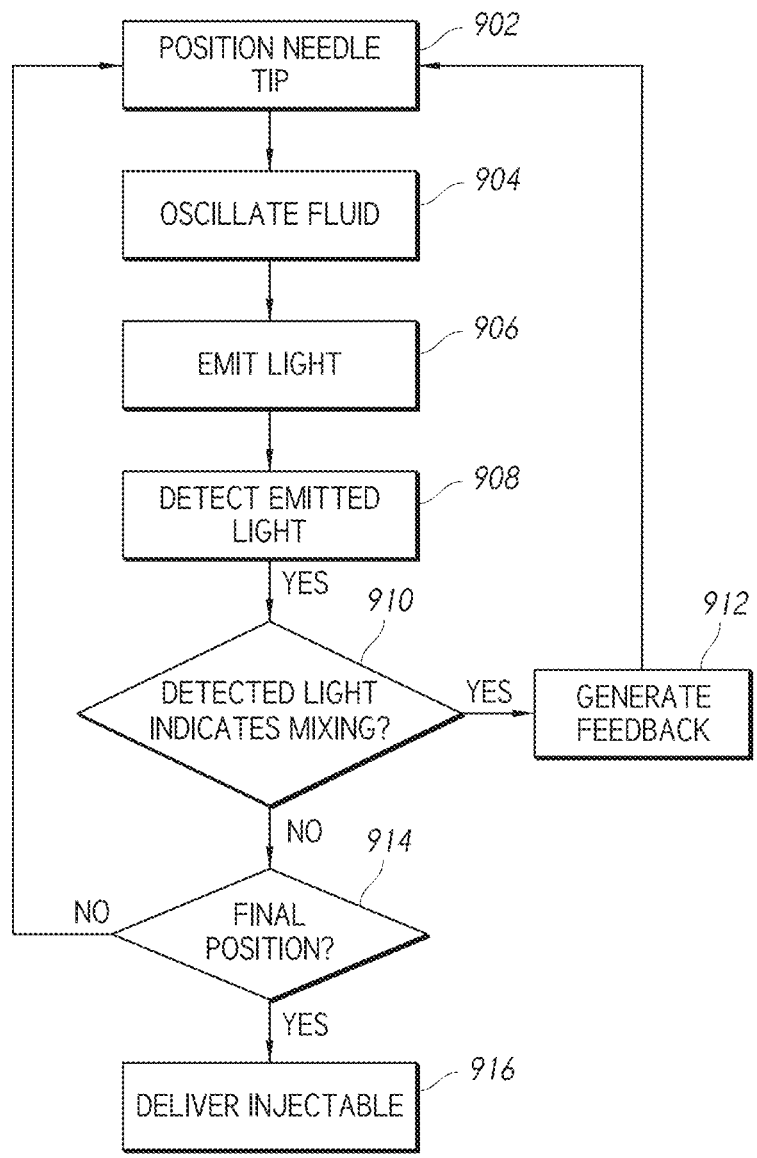
FIG. 9 illustrates a process flow diagram of a method of injection with artery or vein safety.

FIG. 9 illustrates a process flow diagram of a method of injection with artery or vein safety. The method may be implemented in part by the aspirating safety needle 500 described above. At block 902, the needle tip is positioned in the subject. At block 904, fluid is oscillated or otherwise circulated between the needle tip and the aspirating reservoir. At block 906, light is emitted into the aspirating reservoir. At block 908, the emitted light is detected. The detection includes detecting a change in a characteristic of the light indicating the mixing of blood or other fluid with the reservoir fluid. At decision block 910, a determination is made as to whether the detected characteristic of the light indicates mixing of the aspirator reservoir fluid with a fluid of interest such as blood. For example, the aspirator reservoir fluid may be saline and provide a first set of light characteristics (e.g., color, intensity). If blood is mixed with the aspirator reservoir fluid, the light characteristics detected will change. Based on the light characteristics detected and/or the change, mixing may be identified. If mixing is identified, at block 912 feedback is generated. The feedback alerts the needle operator that a vein or artery may be contacted. Based on this feedback, the process may return to block 902 for further needle positioning. If fluid mixing is not detected at block 910, the process continues to determination block 914. At block 914, a determination is made as to whether the needle is in its final position. A final position generally refers to the position at which the injectable substance will be delivered. If it is determined at block 914 that the needle is not in its final position, the process returns to block 902 for further needle positioning. If it is determined at block 914 that the needle is in its final position, at block 916 the injectable substance is delivered.

System for Avoiding Blood Vessels

As described above, it can be useful to determine whether a distal tip of a medical device is positioned in a blood vessel. For example, if the clinician is withdrawing blood, an indication of whether the needle has entered the blood vessel could be useful. As another example, it may be preferable to inject a therapeutic agent in a specific location (e.g., blood vessel, muscle, subcutaneous tissue, or otherwise), thus an indication of whether the needle has indeed entered that layer of tissue could be useful. This information can help improve medical outcomes and patient safety.

Figure 10:
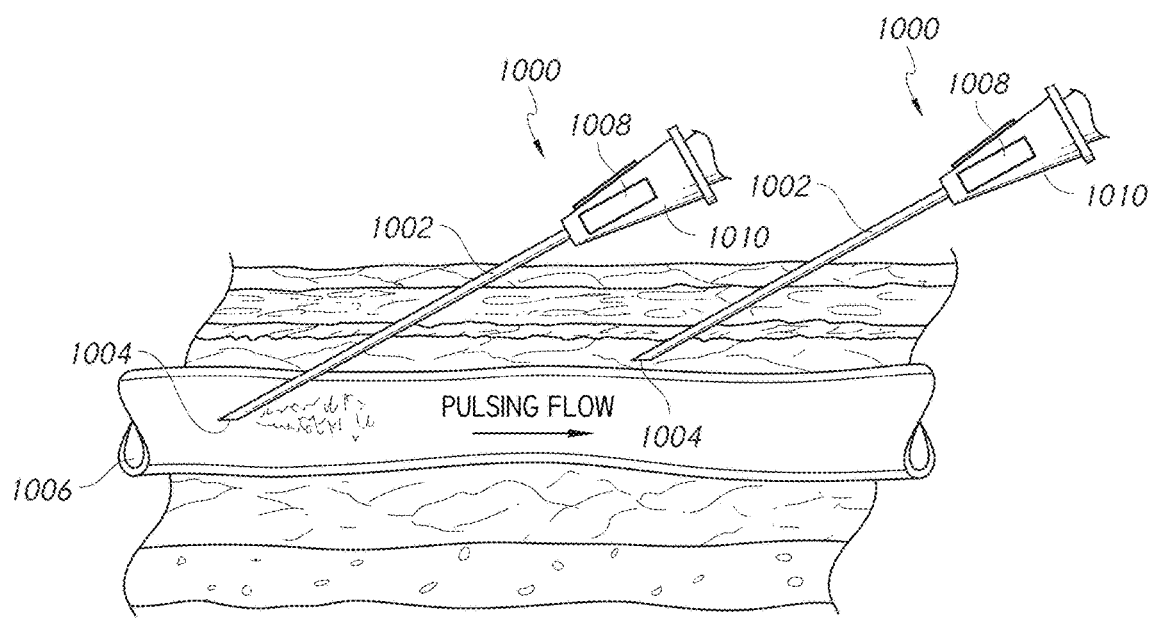
FIG. 10 illustrates a needle-based device positioned in a blood vessel and a needle positioned outside the blood vessel.
Figure 11:
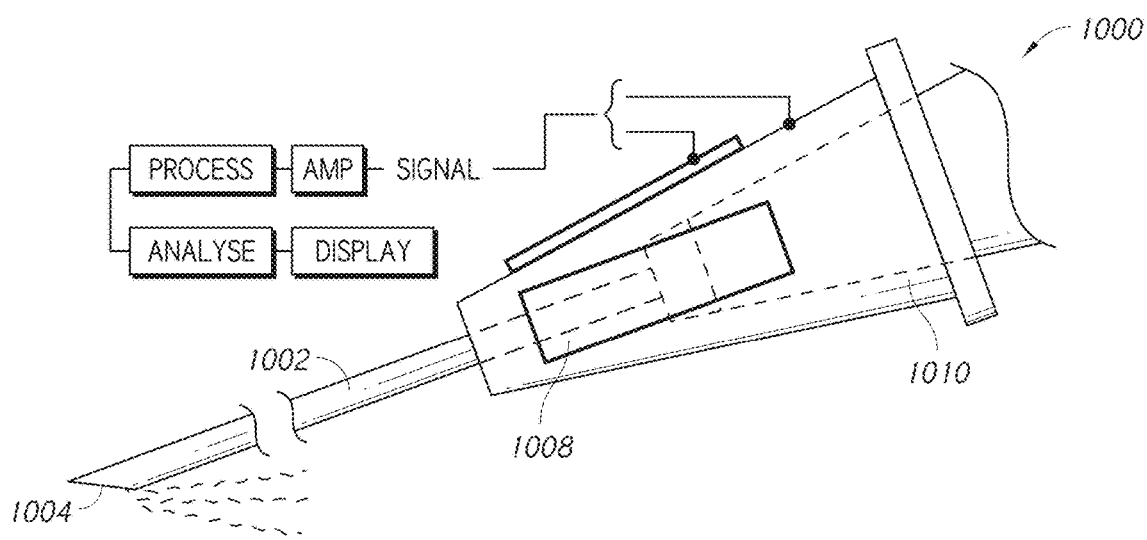
FIG. 11 illustrates an enlarged view of a hub portion of one of the needle-based devices shown in FIG. 10.

FIGS. 10 and 11 illustrate a system 1000 for detecting whether a distal tip of a medical device has entered a blood vessel. In the illustrated example, the system includes a needle-based device 1002. The system can determine whether the distal tip 1004 of the needle 1002 is positioned in a blood vessel 1006 by detecting pressure, motion, vibration, or the like. For example, if turbulent motion is detected at the distal tip 1004 of the needle 1002, then it is likely that the distal tip 1004 of the needle 1002 is in a blood vessel 1006. If less than turbulent motion is detected at the distal tip 1004 of the needle 1002, then it is likely that the distal tip 1004 of the needle 1002 is not within the blood vessel 1006.

In general, system can include one or more sensors 1008 to detect the motion, pressure, and/or vibration. The one or more sensors 1008 can be positioned in a hub 1010 of the needle 1002, any other portion of the needle 1002, or separately connected to the needle 1002. If necessary, the one or more sensors 1008 can be conductively connected to an amplifier magnify the signal. The needle 1002 can display the signal on the device itself or a separate display device connected to the needle (e.g., a tablet, computer screen, or otherwise).

The system can also include one or more processors, which may be integrated with the needle 1002 or separately connected. The processor can be configured to analyze the signal to provide a user-friendly output, such as a binary output indicative of whether or not the distal tip is positioned within a blood vessel. In other configurations, the output can be mapped as described above or displayed using an augmented or virtual reality system as described further below.

Figure 12A:
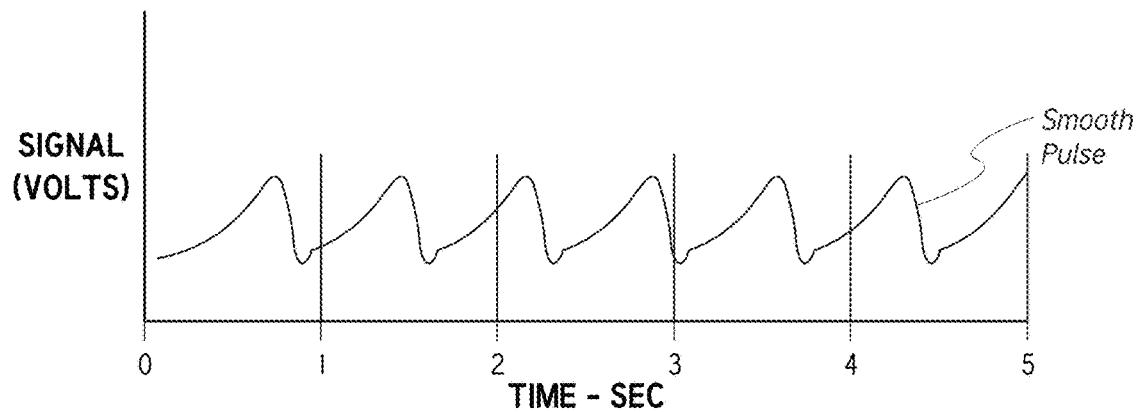
FIGS. 12A and 12B illustrate a waveform indicative of motion at a distal tip of each needle shown in FIG. 10.
Figure 12B:
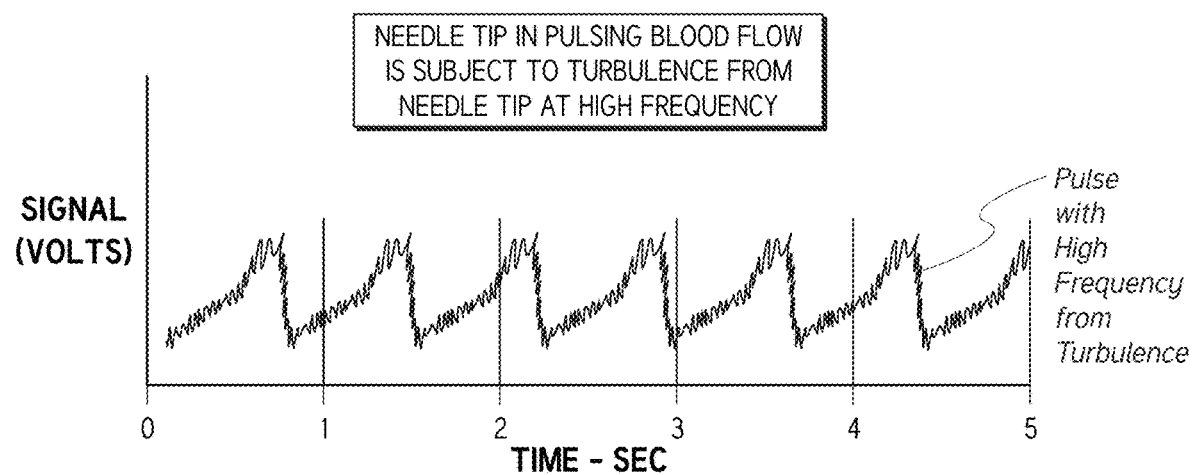

The output can be determined by comparing a frequency of the waveform to a threshold value (see FIGS. 12A and 12B). For example, if the frequency is less than the threshold value, then the distal tip 1004 of the needle 1002 is in the blood vessel 1006 (see FIG. 12B). On the other hand, if the frequency is greater than the threshold value, then the distal tip 1004 of the needle 1002 is not within the blood vessel (see FIG. 12A). In some instances, the threshold value may be determined based on initial readings from the current procedure or readings from a previous procedure. In other instances, the threshold value can be determined based on a patient population.

In the illustrated example, the sensor 1008 is a piezoelectric sensor conductively conducted to an amplifier. The piezoelectric sensor can include pressure and/or acceleration sensing elements to detect motion at the distal tip of the needle. The sensor can generate a signal based on the detected motion. As shown in FIGS. 12A and 12B, if the tip 1004 of the needle 1002 is outside the blood vessel 1006, the sensor 1008 only detects tissue deflection from pulsing blood pressure. In contrast, if the tip 1004 of the needle 1002 is within the blood vessel 1006, the sensor 1008 detects the turbulence of actual blood flow, which has a higher frequency compared to the waveform outside the tissue. The system may output the waveform alone, and/or the system may process this data to provide a user-friendly output as outlined above.

System for Determining Proximity to a Nerve

As described above, it can be useful to determine whether a distal tip of a medical device is close a nerve because actual contact with the never can be painful.

Figure 13:
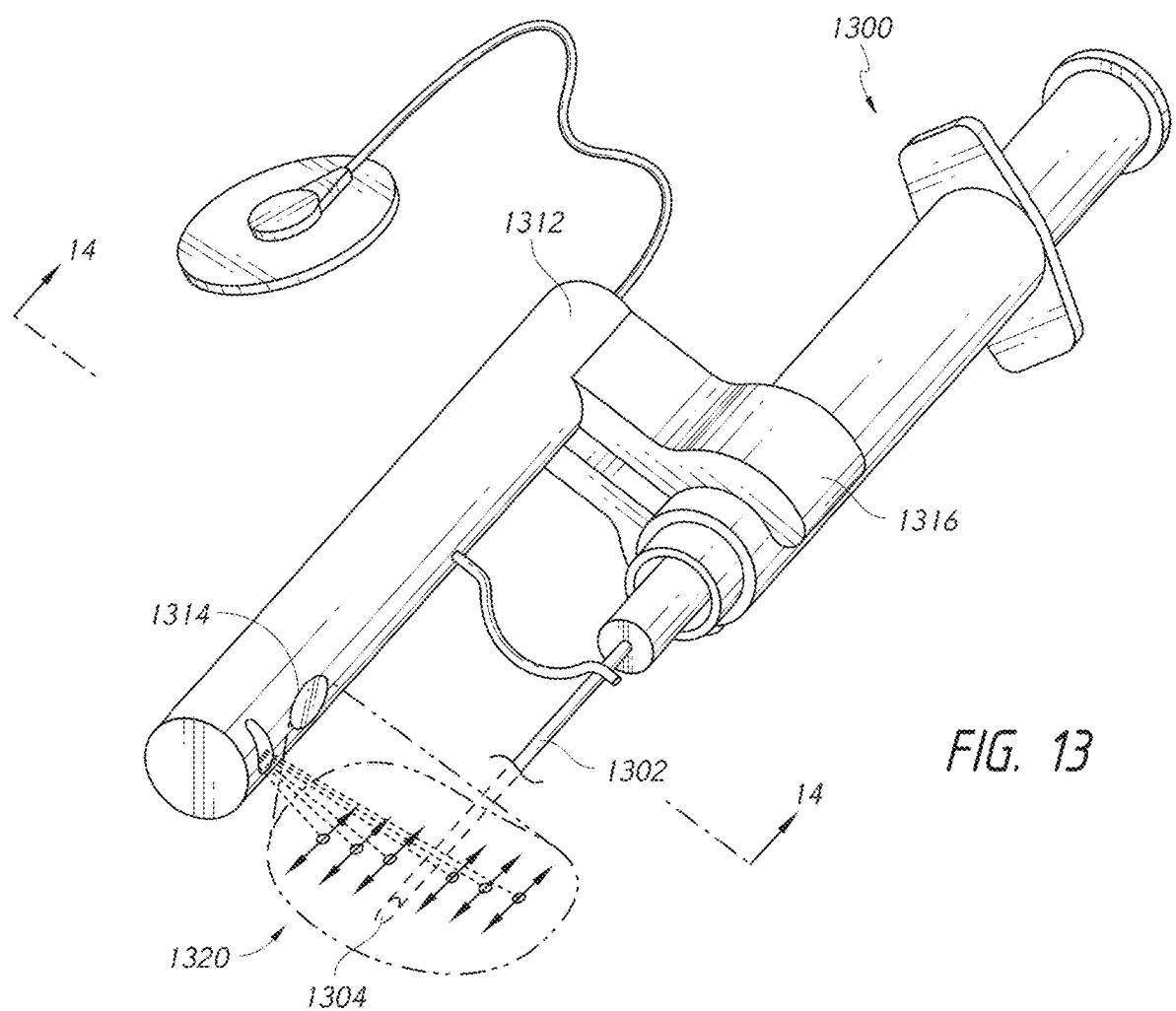
FIG. 13 illustrates a system for detecting the proximity of a nerve to a tip of a needle.
Figure 14:
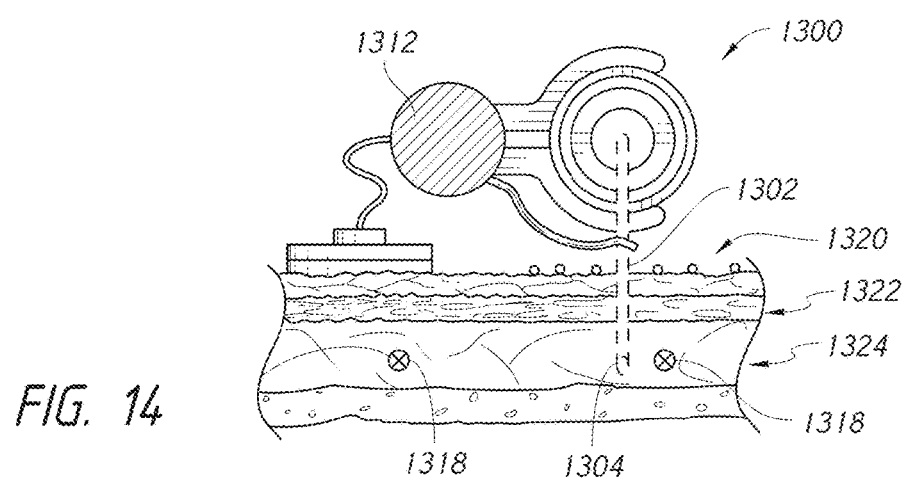
FIG. 14 is a schematic representation of the system in FIG. 13 inserted into the tissue.

FIGS. 13 and 14 illustrate a system for detecting whether a distal tip of a medical device is in proximity to a nerve. In the illustrated example, the system 1300 includes a needle-based device 1302. The system 1300 can determine whether the distal tip 1304 of the needle 1302 is in proximity to a nerve 1318 by assessing a response to an electrical pulse. In general, as the response increases, the distal tip 1304 of the needle is 1302 closer to a nerve 1318.

The system 1300 can include a pulse generator 1312 separately connected to the needle-based device 1302 and one or more sensors 1314 (e.g., motion detector) for detecting a response to the generated pulse. The pulse generator 1312 and the one or more sensors 1314 can be positioned in the same housing or be separate devices. The system 1300 can output the signal generated by the one or more sensors 1314. The system 1300 can also include one or more processors, which can be integrated with the needle 1302 or separately connected. The processor can be configured to analyze the signal generated from the response to provide a user-friendly output indicative of how close the distal tip is to a nerve. The user-friendly output can be a numerical distance or a scaled output (e.g., color scale or numerical scale) proportional to the proximity of the distal tip to the nerve. In some implementations, the output can be a binary indication of whether to continue advancing the needle or whether to inject the therapeutic agent. In other configurations, the output can be mapped as described above or displayed using an augmented or virtual reality system as described further below.

The system can be configured based on data from an initial reading from the current procedure or a reading from a previous procedure. Alternatively, the system can be configured based on data from a patient population. The system can provide the output by comparing the generated response to a threshold value indicative of being too close to a nerve. The system can output the indication to a display device that can be part of the medical device, the pulse generator, the pulse detector, or a separate component.

In the illustrated example, the system includes a pulse generator 1312 configured to supply a small electrical current to the needle 1302 or otherwise supply a small current to the patient to assess nerve response. The pulse generator 1312 can be a separate component connected to the needle-based device 1302 using a clip 1316. When the pulse generator 1312 is connected to the needle-based device 1302, the pulse generator can extend distally toward a distal tip 1304 of the needle 1302. The system 1300 can also include a mechanism for detecting a response to the pulse (e.g., a motion detector). This detection mechanism can be in the same housing as the pulse generator 1312. As shown in FIG. 4, the pulse detection mechanism can assess a physiological response to the generated pulse by outputting a visual indicator, such as a light pattern 1320, on the patient's skin 1322 and detecting movement of the light pattern 1320. When the pulse is applied to the patient, the muscles 1324 will flex, which will cause the light pattern 1320 to move. As the distal tip 1304 of the needle 1302 moves closer to a nerve 1318, the muscle flexure increases, which causes increased light pattern movement. In other embodiments, the visual indicator might be directly applied to the skin (e.g., using ink or adhesive), and the motion detector 1314 will detect movement of the visual indicator.

The system 1300 can output a signal indicative of the level of movement, and/or the system can process this data to provide a user-friendly output as outlined above.

System for Determining Depth

In some treatments, it may be useful to understand the distance between the distal tip of a medical device and the patient's skin, for example to increase the efficacy of an injected therapeutic agent. It may also be useful to understand the distance between the distal tip of the medical device and the patient's bone to avoid hurting the patient.

Figure 15:
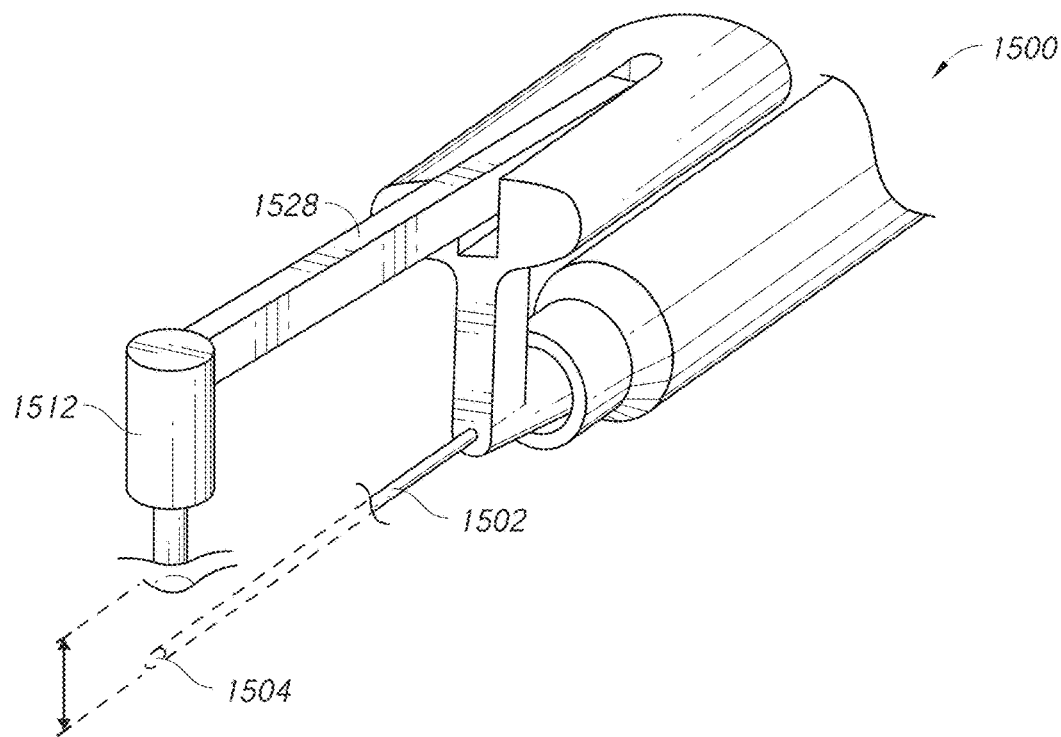
FIG. 15 illustrates a system for detecting needle depth.
Figure 16:
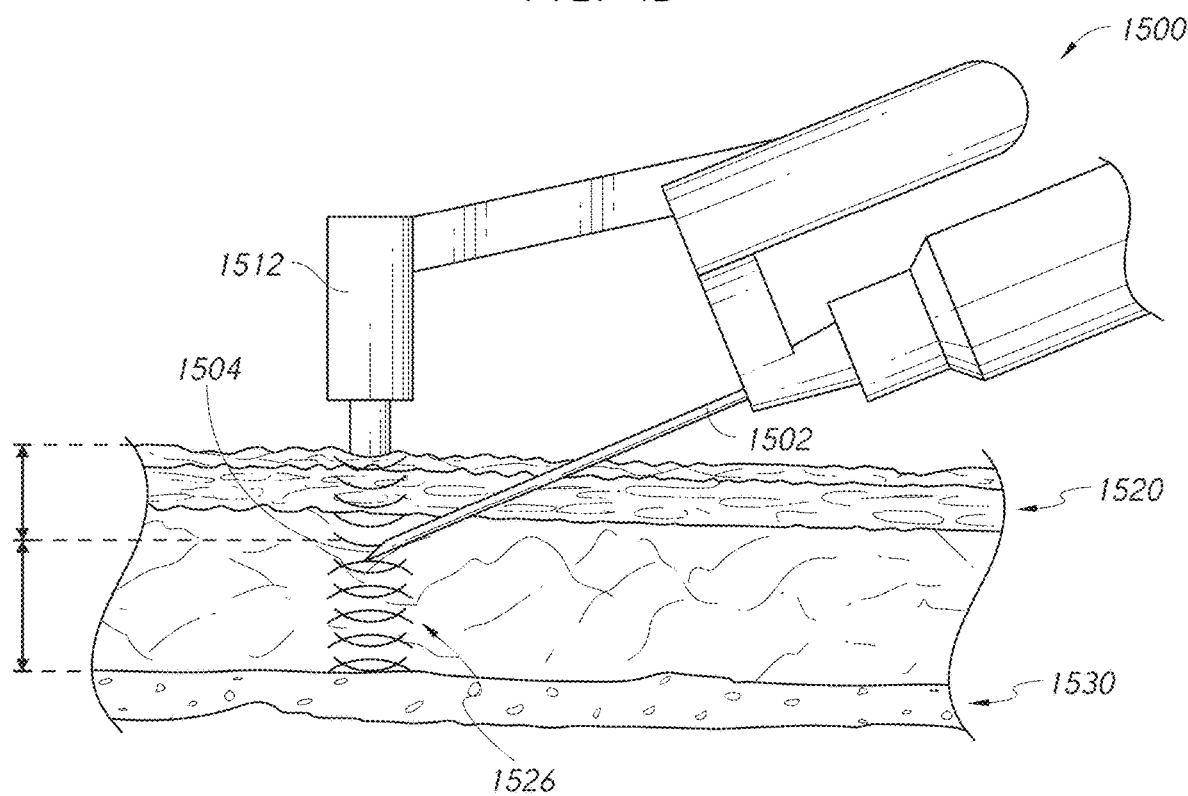
FIG. 16 illustrates the system in FIG. 15 inserted into live tissue.

FIGS. 15 and 16 illustrate a system for determining the distance between the distal tip of a medical device and the patient's skin and/or between the distal tip of the medical device and the patient's bone. The system 1500 can include a pulse generator 1512 separately connected to the needle-based device 1502 and one or more sensors (not shown) for detecting a response to the generated pulse 1526. The system 1500 can include one or more processors, which may be integrated with the needle 1502 or separately connected. The processor can be configured to analyze the signal generated from the response to provide a user-friendly output indicative of a distance between a distal tip of the needle to the patient's skin and/or the patient's bone. The system 1500 can output the distance to a display device (not shown) that may be part of the medical device, the pulse generator, or a separate component. In some configurations, the output can be mapped as described above or displayed using an augmented or virtual reality system as described further below.

In the illustrated example, the system 1500 includes a pulse generator 1512 configured to apply a mechanical pulse 1526 by tapping the patient's skin 1520. The pulse generator 1512 can include a body removably or permanently mounted to the needle-based device 1502. A spring-loaded arm 1528 can extend from the body and toward a distal tip 1504 of the needle 1502. When the spring-loaded arm 1528 moves, a distal portion of the pulse generator 1512 can tap the patient's skin 1520 near the needle tip 1504. A vibration sensor (not shown) can be configured to detect vibrations in the needle 1502 in response to the pulse generator 1512. The vibration sensor can be positioned in a hub portion (not shown) of the needle 1502. A processing unit can perform a process that determines a time delay between the application of the mechanical pulse 1526 and the receipt of a signal indicative of needle vibration. Based on the time delay, the process can determine a distance between the distal tip of the needle and the patient's skin. The distance can be determined using math modeling or by comparing the time delay to a threshold value for that specific patient or from a patient population. The processor may be configured to discount the signal or time delay using baseline data indicative of baseline vibrations from the patient's pulse. The system 1500 can output the distance to a display device (not shown) on the needle-based device 1502 or separate from the needle-based device 1502 (e.g., using mapping, virtual reality, augmented reality, or otherwise).

In some implementations, the vibration sensor may detect secondary vibrations as the mechanical pulse 1526 reflects off the bone 1530 and toward the tip 1504 of the needle 1502. The processing unit can determine a time delay between the application of the mechanical pulse and receipt of a signal indicative of the secondary vibrations, or determine a time delay between receipt of the first signal from the initial vibrations and receipt of the second signal from the secondary vibrations. The processing unit can perform a process to determine a distance between the distal tip 1504 of the needle 1502 and the bone 1530 based on this second time delay. The distance can be determined using math modeling or by comparing the second time delay to a threshold value for that specific patient or from a patient population. The system 1500 can output the numerical distance to a display device (not shown) on the needle-based device 1502 or separate from the needle-based device 1502 (e.g., using mapping, virtual reality, augmented reality, or otherwise).

Virtual Reality System

Figure 17:
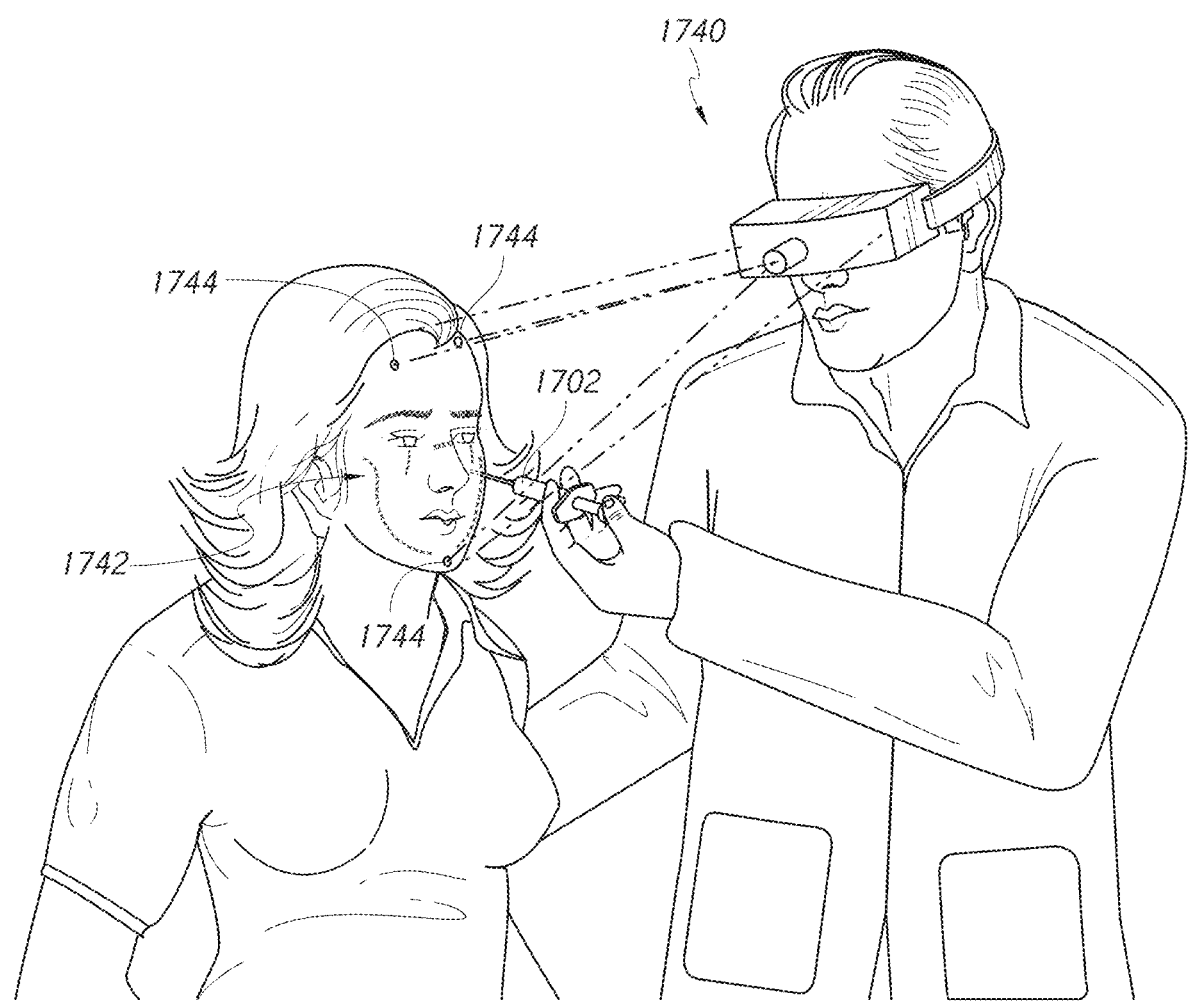
FIG. 17 illustrates use of a virtual reality system for guiding a syringe.

As shown in FIG. 17, an augmented or virtual reality display 1740 (e.g., wearable glasses or as otherwise described above) can be used to overlay a computer-generated three-dimensional image 1742 on a patient. The computer-generated image(s) 1742 can correspond to one or more layers of anatomy (e.g., bones, nerves, blood vessels, or the like) for that specific patient. The images can be obtained using a CT scan, an MRI scan, a photographic image, an X-ray, the physiological detection methods described above, or other imaging systems.

Figure 18:
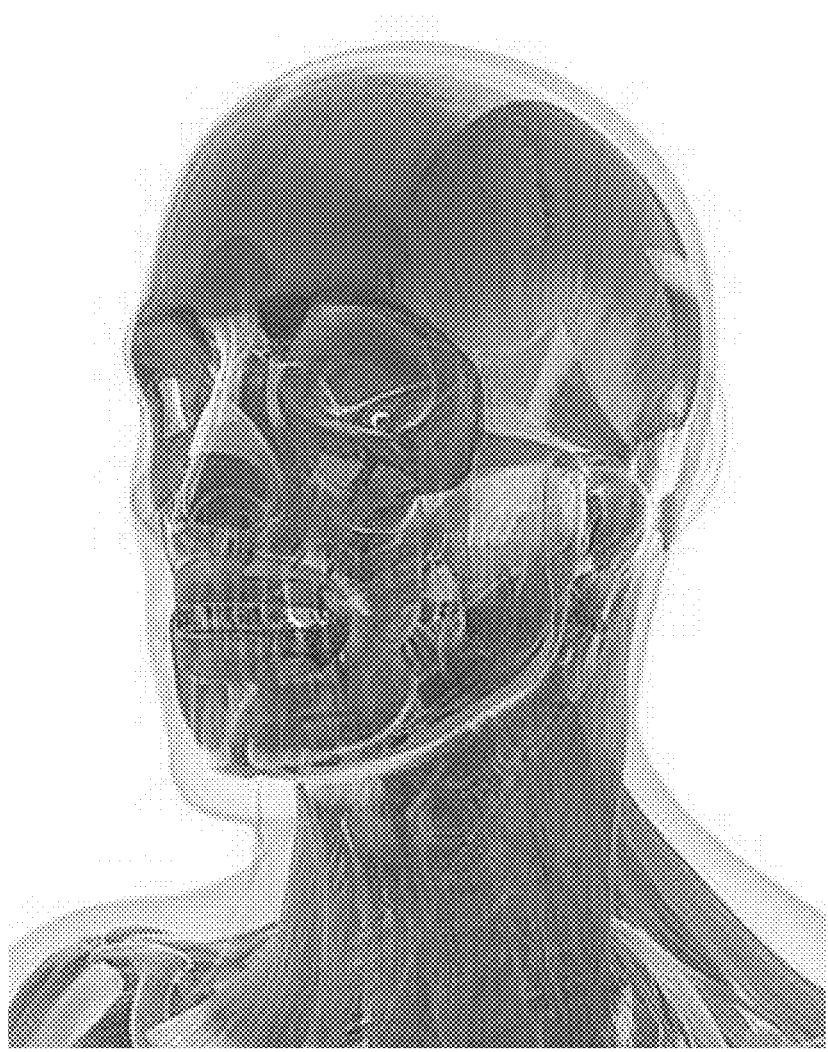
FIG. 18 illustrates an example of a three-dimensional image that can be seen through the virtual reality system.

FIG. 18 illustrates an example of an image 1742 that can be seen on the display 1740. This image 1742 can be aligned with the patient's face using one or more alignment targets 1744. For example, these alignment targets 1744 can be anatomical features, such as the center of an eyeball or an apex of the nose. As another example, these targets 1744 can be alignment markers (e.g., reflective beads) that can be positioned on the patient when the MRI image is captured, such that the markers appear in the MRI image(s). As shown in FIG. 17, a plurality of markers 1744 can be positioned around an outer periphery of the patient's face. These alignment markers 1744 can remain on the patient or be positioned again on the patient in the same location for the actual procedure. During the procedure, the clinician can align the markers in the computer generated image 1742 with the markers 1744 on the patient's face. In some implementations, the display system 1700 can include a camera that captures the location of the alignment markers 1744 during the actual procedure and automatically aligns the markers in the computer generated image 1742 with the markers 1744 on the patient's face.

When this image 1742 is meshed with the patient, the locations of structures in the image 1742 correspond to the actual location of those structures in the patient. The ability to visualize the tissue layers as the clinician is performing a procedure can help the clinician perform the procedure at an optimal location. For example, this system can be used to guide a needle-based device 1702 to an appropriate depth (e.g., for a therapeutic injection). The movement of the needle-based device 1702 can be seen on the display device 1702. Thus, as the needle-based device 1702 is moved through the actual patient, the location of the distal tip of the needle-based device 1702 can be seen on the computer-generated image 1742. When the distal tip of the needle-based device 1702 is positioned in the target location in the image 1742, the distal tip of the needle-based device 1702 is positioned in the target location in the actual patient.

Terminology

One or more of the above-described features that can be incorporated into a medical device to determine a position of the medical device in living tissue and/or display the physiological feature.

Certain examples described herein are discussed with respect to a needle, but the needle can be any needle-based device, such as a standard needle, syringe, biopsy needle, aspiration needle, or the like. Further, the examples can be applied to other medical devices inserted into patients, such as catheters, gastric feeding tubes, tracheostomy tubes, or other medical devices.

It should be understood that the medical devices can be used in the face, shoulder, knee, spine, or any other part of the anatomy of a human or animal.

The word "exemplary" is used herein to mean "serving as an example, instance, or illustration." Any embodiment described herein as "exemplary" is not necessarily to be construed as preferred or advantageous over other embodiments. Various aspects of the novel systems, apparatuses, and methods are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein, one skilled in the art may appreciate that the scope of the disclosure is intended to cover any aspect of the novel systems, apparatuses, and methods disclosed herein, whether implemented independently of, or combined with, any other aspect described. For example, an apparatus may be implemented or a method may be practiced using any number of the aspects set forth herein. In addition, the scope of the described features is intended to cover such an apparatus or method which is practiced using other structure, functionality, or structure and functionality in addition to or other than the various aspects of the invention set forth herein. It may be understood that any aspect disclosed herein may be embodied by one or more elements of a claim.

Although particular aspects are described herein, many variations and permutations of these aspects fall within the scope of the disclosure. Although some benefits and advantages of the preferred aspects are mentioned, the scope of the disclosure is not limited to particular benefits, uses, or objectives. Rather, aspects of the disclosure are broadly applicable to different injection training technologies, system configurations, networks, and transmission protocols, some of which are illustrated by way of example in the figures and the included description of the preferred aspects. The detailed description and drawings are merely illustrative of the disclosure rather than limiting, the scope of the disclosure being defined by the appended claims and equivalents thereof.

The terms "processor" and "processor module," as used herein are a broad terms, and are to be given their ordinary and customary meaning to a person of ordinary skill in the art (and are not to be limited to a special or customized meaning), and refer without limitation to a computer system, state machine, processor, or the like designed to perform arithmetic or logic operations using logic circuitry that responds to and processes the basic instructions that drive a computer. In some embodiments, the terms can include ROM and/or RAM associated therewith.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing, and the like.

As used herein, the term "message" encompasses a wide variety of formats for transmitting information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed/transmitted/stored/received/etc. in multiple parts.

Any reference to an element herein using a designation such as "first," "second," and so forth does not generally limit the quantity or order of those elements. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may include one or more elements.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The methods disclosed herein include certain actions taken by a practitioner; however, they can also include any third-party instruction of those actions, either expressly or by implication. For example, actions such as "inserting the testing tool" include "instructing insertion of a testing tool."

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such embodiment decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the disclosures described herein can be embodied within a form that does not provide all of the features and benefits set forth herein, as some features can be used or practiced separately from others. The scope of certain disclosures disclosed herein is indicated by the appended claims rather than by the foregoing description. All changes which come within the meaning and range of equivalency of the claims are to be embraced within their scope.

What is claimed is:

1. A system for determining whether a medical device is within a blood vessel during a procedure, the system comprising:
   a needle comprising a distal tip;
   a hub at a proximal end of the needle, the hub comprising a sensor for detecting motion at the distal tip of the needle, the sensor configured to generate a signal based on the detected motion; and
   a processing unit configured to perform a process, the process comprising:
      comparing a frequency of the signal to a threshold value; and
      providing an indication of whether the distal tip of the needle is in the blood vessel based on the comparison between the frequency of the signal and the threshold value.

2. The system of claim 1, further comprising a display configured to display the indication of whether the distal tip of the needle is in the blood vessel.

3. The system of claim 2, wherein the hub comprises the display.

4. The system of claim 2, wherein the indication is a binary output indicative of whether the distal tip of the needle is in the blood vessel.

5. The system of claim 2, wherein the indication is a waveform indicative of the detected motion at the distal tip of the needle.

6. The system of claim 2, wherein the display is an augmented reality display.

7. The system of claim 2, wherein the display is a virtual reality display.

8. The system of claim 2, wherein the display is wearable glasses.

9. The system of claim 2, wherein the display is configured to display movement of the distal tip of the needle.

10. The system of claim 1, wherein the sensor is a piezoelectric sensor.

11. The system of claim 1, wherein the threshold value is patient specific.

12. The system of claim 1, further comprising an amplifier configured to amplify the signal generated by the sensor.

13. The system of claim 1, wherein the processing system is configured to generate a virtual environment comprising a graphical representation of the blood vessel based on the detected motion, by the sensor, at the distal tip of the needle.

14. The system of claim 13, further comprising a display device configured to overlay the graphical representation on a patient.

\* \* \* \* \*